US011944579B2

(12) United States Patent
Sankai

(10) Patent No.: US 11,944,579 B2
(45) Date of Patent: Apr. 2, 2024

(54) BIOLOGICAL ACTIVITY DETECTION APPARATUS AND BIOLOGICAL ACTIVITY DETECTION SYSTEM

(71) Applicants: CYBERDYNE Inc., Tsukuba (JP); University of Tsukuba, Tsukuba (JP)

(72) Inventor: Yoshiyuki Sankai, Ibaraki (JP)

(73) Assignees: CYBERDYNE Inc., Tsukuba (JP); University of Tsukuba, Tsukuba (JP)

(*) Notice: Subject to any disclaimer, the term of this patent is extended or adjusted under 35 U.S.C. 154(b) by 657 days.

(21) Appl. No.: 16/327,806

(22) PCT Filed: Aug. 24, 2017

(86) PCT No.: PCT/JP2017/030393
§ 371 (c)(1),
(2) Date: Feb. 22, 2019

(87) PCT Pub. No.: WO2018/038225
PCT Pub. Date: Mar. 1, 2018

(65) Prior Publication Data
US 2019/0183713 A1    Jun. 20, 2019

(30) Foreign Application Priority Data

Aug. 24, 2016  (JP) ................. 2016-164009

(51) Int. Cl.
*A61H 3/00* (2006.01)
*A61B 5/291* (2021.01)
(Continued)

(52) U.S. Cl.
CPC .......... *A61H 1/0262* (2013.01); *A61B 5/291* (2021.01); *A61B 5/296* (2021.01); *A61B 5/344* (2021.01);
(Continued)

(58) Field of Classification Search
CPC .......... A61H 1/0262; A61H 3/00; A61H 1/00; A61H 2003/007; A61H 2201/5007;
(Continued)

(56) References Cited

U.S. PATENT DOCUMENTS 5,291,888 A * 3/1994 Tucker .................. A61B 5/291
600/383
9,120,227 B2 * 9/2015 Zheng .................. B62D 57/032
(Continued)

FOREIGN PATENT DOCUMENTS

EP    2417941 A1    2/2012
EP    3031500 A1 * 6/2016 ........... A63B 21/285
(Continued)

OTHER PUBLICATIONS

Machine translation of specification and claims for JP2012161375A (Year: 2012).*
(Continued)

*Primary Examiner* — Michael R Reid
*Assistant Examiner* — Tyler A Raubenstraw
(74) *Attorney, Agent, or Firm* — Procopio, Cory, Hargreaves & Savitch LLP

(57) ABSTRACT

A biological activity detection apparatus includes: a drive unit that actively or passively drives in conjunction with a limb motion of a subject; a periarticular detection unit that detects a periarticular physical quantity around a joint in association with the limb motion of the subject based on an output signal from the drive unit; a biological signal detection unit located at a body surface site of the subject with reference to the joint and includes an electrode group for detecting a biological signal of the subject, wherein an activity status of a musculoskeletal system and/or a transmission status of a peripheral nervous system around the joint are converted into quantitative musculoskeletal system
(Continued)

data and/or nervous system data on the basis of the physical quantity acquired from the periarticular detection unit and a myogenic potential signal and a neural transmission signal which are acquired from the biological signal processing unit.

16 Claims, 9 Drawing Sheets

(51) Int. Cl.
  *A61B 5/296*    (2021.01)
  *A61B 5/344*    (2021.01)
  *A61B 5/389*    (2021.01)
  *A61B 10/00*    (2006.01)
  *A61F 2/72*     (2006.01)
  *A61H 1/02*     (2006.01)
  *B25J 9/00*     (2006.01)
  *B25J 11/00*    (2006.01)
  *B25J 13/08*    (2006.01)
  *B25J 19/02*    (2006.01)

(52) U.S. Cl.
  CPC .............. *A61B 5/389* (2021.01); *A61B 10/00* (2013.01); *A61F 2/72* (2013.01); *A61H 3/00* (2013.01); *B25J 9/0006* (2013.01); *B25J 11/00* (2013.01); *B25J 13/08* (2013.01); *B25J 19/02* (2013.01); *A61B 2505/09* (2013.01); *A61H 2003/007* (2013.01); *A61H 2201/1626* (2013.01); *A61H 2201/1642* (2013.01); *A61H 2201/1652* (2013.01); *A61H 2201/5007* (2013.01); *A61H 2201/5061* (2013.01); *A61H 2230/085* (2013.01); *A61H 2230/105* (2013.01)

(58) Field of Classification Search
  CPC .... A61H 2201/5061; A61H 2201/1642; A61H 2201/1626; A61H 2230/085; A61H 2201/1652; A61H 2230/105; B25J 9/0006; B25J 13/08; B25J 11/00; B25J 19/02; A61B 5/00–7945; A61B 5/296; A61B 5/291; A61B 2505/09; A61B 5/344; A61B 5/389; A61B 10/00; A61F 2/72

See application file for complete search history.

(56) References Cited

U.S. PATENT DOCUMENTS

| | | | |
|---|---|---|---|
| 9,186,479 B1* | 11/2015 | Franceschetti | A61B 5/11 |
| 9,351,900 B2* | 5/2016 | Walsh | A63B 23/0355 |
| 9,527,214 B2* | 12/2016 | Kondo | B25J 9/1697 |
| 9,943,458 B2* | 4/2018 | Tanaka | A61F 5/0125 |
| 10,285,617 B2* | 5/2019 | Toth | A61B 5/296 |
| 10,638,927 B1* | 5/2020 | Beard | A61H 9/0078 |
| 2005/0143785 A1 | 6/2005 | Libbus | |
| 2008/0161937 A1 | 7/2008 | Sankai | |
| 2008/0234608 A1 | 9/2008 | Sankai | |
| 2008/0255479 A1* | 10/2008 | Wilkins | A63B 23/035 601/5 |
| 2008/0294033 A1* | 11/2008 | Yamazaki | A61B 5/6814 600/407 |
| 2008/0306397 A1* | 12/2008 | Bonmassar | A61B 5/6814 600/544 |
| 2009/0099473 A1* | 4/2009 | Dunseath | A61B 5/6814 600/383 |
| 2010/0152629 A1* | 6/2010 | Haas, Jr. | A63B 21/4011 601/34 |
| 2010/0198115 A1 | 8/2010 | Koeneman et al. | |
| 2010/0280628 A1* | 11/2010 | Sankai | A61F 5/0102 623/25 |
| 2011/0118564 A1 | 5/2011 | Sankai | |
| 2011/0166491 A1* | 7/2011 | Sankai | A41D 13/1281 601/84 |
| 2011/0224530 A1* | 9/2011 | David | A61B 5/021 600/388 |
| 2012/0014580 A1 | 1/2012 | Blum et al. | |
| 2012/0172682 A1* | 7/2012 | Linderman | A61B 5/389 600/300 |
| 2012/0242501 A1* | 9/2012 | Tran | A61B 5/0024 340/870.02 |
| 2012/0310050 A1* | 12/2012 | Osorio | G16H 20/40 600/300 |
| 2013/0211594 A1* | 8/2013 | Stephens, Jr. | B25J 9/1689 700/258 |
| 2013/0281798 A1* | 10/2013 | Rau | A61B 5/165 600/595 |
| 2014/0135593 A1* | 5/2014 | Jayalth | G09B 19/0038 600/301 |
| 2014/0171838 A1* | 6/2014 | Aleksov | A61H 3/00 601/33 |
| 2014/0213874 A1* | 7/2014 | Tong | A61B 5/291 600/383 |
| 2014/0236257 A1 | 8/2014 | Parker et al. | |
| 2014/0277739 A1* | 9/2014 | Kornbluh | F16D 28/00 29/428 |
| 2014/0330186 A1* | 11/2014 | Hyde | A61F 2/70 602/19 |
| 2014/0358290 A1* | 12/2014 | Kazerooni | G06F 3/011 700/275 |
| 2015/0088038 A1* | 3/2015 | Fukunaga | A61H 1/005 600/595 |
| 2015/0100251 A1* | 4/2015 | Solinsky | A61B 5/112 702/33 |
| 2015/0112712 A1* | 4/2015 | Murakami | G16H 50/20 705/2 |
| 2015/0134080 A1* | 5/2015 | Roh | B25J 9/1694 623/32 |
| 2015/0148619 A1* | 5/2015 | Berg | A61B 5/6804 600/300 |
| 2015/0196449 A1* | 7/2015 | Ahn | A61H 3/00 623/27 |
| 2015/0224013 A1* | 8/2015 | Kwon | A61H 1/0262 482/51 |
| 2015/0257902 A1* | 9/2015 | Martin | A61F 2/6607 623/47 |
| 2015/0257967 A1* | 9/2015 | Simmons | G16H 50/20 434/236 |
| 2015/0282760 A1* | 10/2015 | Badower | A61B 5/6803 600/383 |
| 2015/0313496 A1* | 11/2015 | Connor | A61B 5/369 600/301 |
| 2015/0327805 A1 | 11/2015 | Ben-Haim | |
| 2015/0366504 A1* | 12/2015 | Connor | A61B 5/6804 600/301 |
| 2016/0008206 A1* | 1/2016 | Devanaboyina | A61H 7/007 601/136 |
| 2016/0015289 A1* | 1/2016 | Simon | A61B 5/6826 600/301 |
| 2016/0022167 A1* | 1/2016 | Simon | A61B 5/4064 600/301 |
| 2016/0045751 A1* | 2/2016 | Jiang | A61B 5/389 607/59 |
| 2016/0143554 A1* | 5/2016 | Lim | A61B 5/6803 600/386 |
| 2016/0166207 A1* | 6/2016 | Falconer | A61B 5/486 600/300 |
| 2016/0242986 A1* | 8/2016 | Nagata | A61H 3/00 |
| 2016/0242987 A1* | 8/2016 | Nagata | A61H 1/0277 |
| 2016/0274162 A1* | 9/2016 | Freeman | A61N 1/39 |
| 2016/0287463 A1* | 10/2016 | Yue | A61H 1/0244 |
| 2016/0331620 A1* | 11/2016 | Kazanchyan | A61N 1/36003 |
| 2016/0338644 A1* | 11/2016 | Connor | A61B 5/1126 |
| 2016/0346539 A1* | 12/2016 | Atsumi | A61N 1/0452 |
| 2016/0354005 A1* | 12/2016 | Oakley | A61B 5/6803 |
| 2017/0056275 A1* | 3/2017 | Lee | A61F 2/72 |
| 2017/0065440 A1* | 3/2017 | Ha | B25J 9/0006 |

(56) References Cited

U.S. PATENT DOCUMENTS

| | | | |
|---|---|---|---|
| 2017/0113015 A1 | 4/2017 | Kaneko | |
| 2017/0143517 A1* | 5/2017 | Sankai | A61F 2/60 |
| 2017/0164893 A1* | 6/2017 | Narayan | A61B 5/14539 |
| 2017/0188830 A1* | 7/2017 | Sankai | A61B 5/7225 |
| 2017/0347906 A1* | 12/2017 | Intrator | A61B 5/7264 |
| 2017/0360360 A1* | 12/2017 | Alqurashi | A61B 5/746 |

FOREIGN PATENT DOCUMENTS

| | | | | |
|---|---|---|---|---|
| JP | 2005095561 A | | 4/2005 | |
| JP | 4178187 B2 | | 9/2008 | |
| JP | 4200492 B2 | | 10/2008 | |
| JP | 2009060946 A | | 3/2009 | |
| JP | 5060304 B2 | | 8/2012 | |
| JP | 2012161375 A | * | 8/2012 | |
| JP | 5283700 B2 | | 6/2013 | |
| JP | 2013179966 A | | 9/2013 | |
| JP | 5409637 B2 | | 11/2013 | |
| JP | 2014-008071 A | | 1/2014 | |
| JP | 2014023795 A | | 2/2014 | |
| JP | 2014523261 A | | 9/2014 | |
| JP | 5830090 B2 | | 10/2015 | |
| JP | 2016513526 A | | 5/2016 | |
| WO | WO-2006105621 A1 | * | 10/2006 | ........... A61B 5/0002 |
| WO | WO-2008044187 A1 | * | 4/2008 | ......... A41D 13/1281 |
| WO | WO-2013033669 A2 | * | 3/2013 | ............... A61F 2/50 |
| WO | 2015/152122 A1 | | 10/2015 | |
| WO | WO-2015164421 A1 | * | 10/2015 | ............. A61B 5/112 |
| WO | 2015199086 A1 | | 12/2015 | |
| WO | WO-2016005367 A1 | * | 1/2016 | ........... A61B 5/1116 |
| WO | WO-2016028888 A1 | * | 2/2016 | ......... A61B 5/04017 |
| WO | WO-2016110804 A1 | * | 7/2016 | ............... A61B 3/16 |
| WO | WO-2016149751 A1 | * | 9/2016 | ........... A61B 5/0816 |
| WO | WO-2016207471 A1 | * | 12/2016 | ........... A61B 5/0004 |

OTHER PUBLICATIONS

International Search Reporting for related PCT App No. PCT/JP2017/030393 dated Sep. 19, 2017, 13 pgs.

Extended European Search Report dated Jan. 29, 2020 for related EP App No. 17843701.8 dated 11 pgs.

European Patent Office, Office Action, Application No. 17 843 701.8-1113, dated Jul. 22, 2021, in 10 pages.

European Patent Office, Office Action, Application No. 17 843 701.8-1113, dated May 30, 2023, in 10 pages.

* cited by examiner

FIG. 6
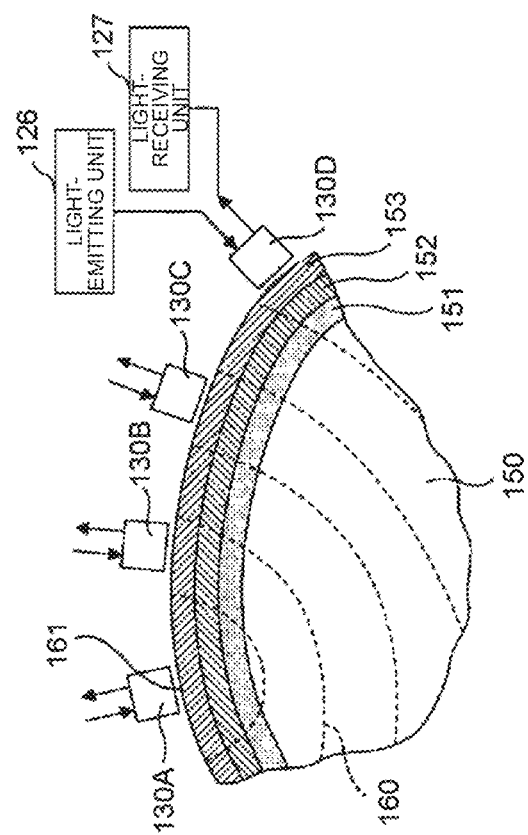
(A)
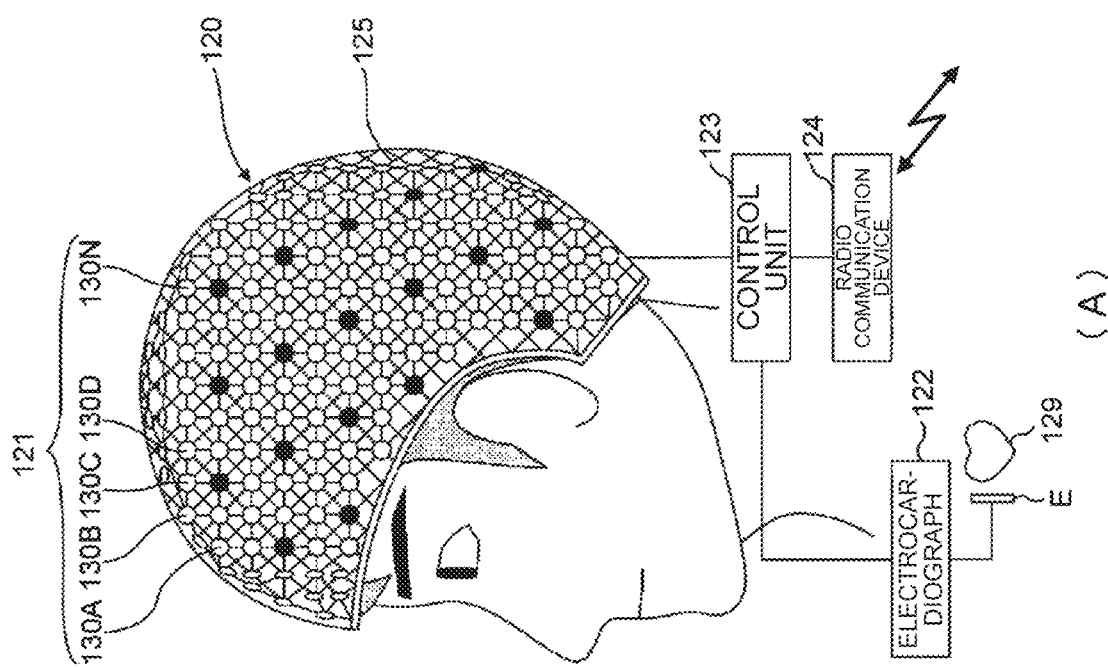
(B)

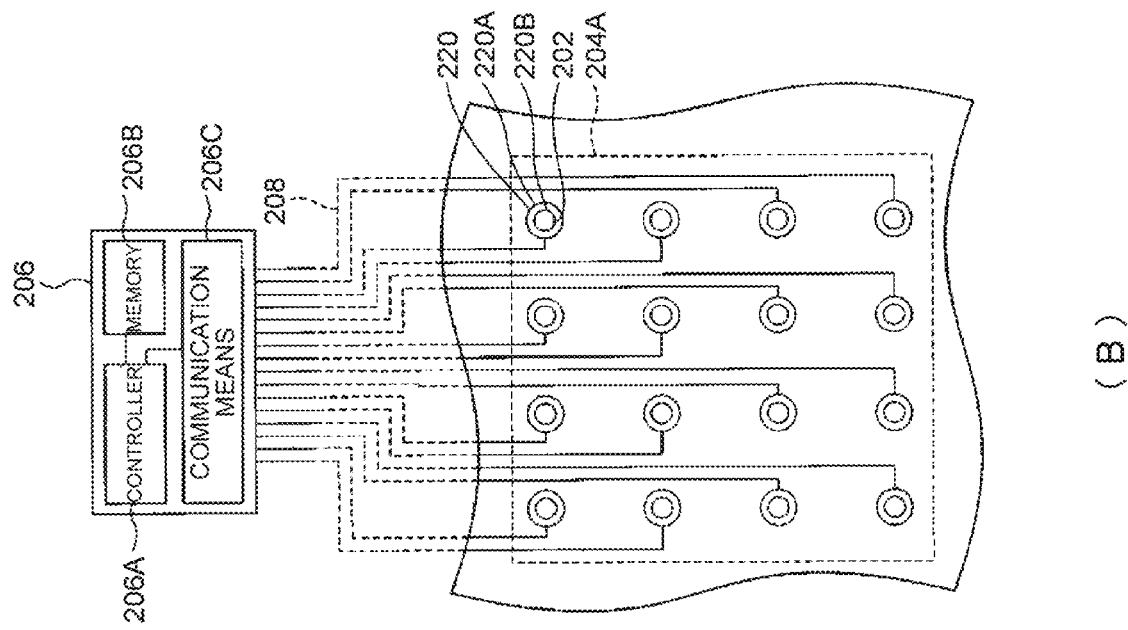
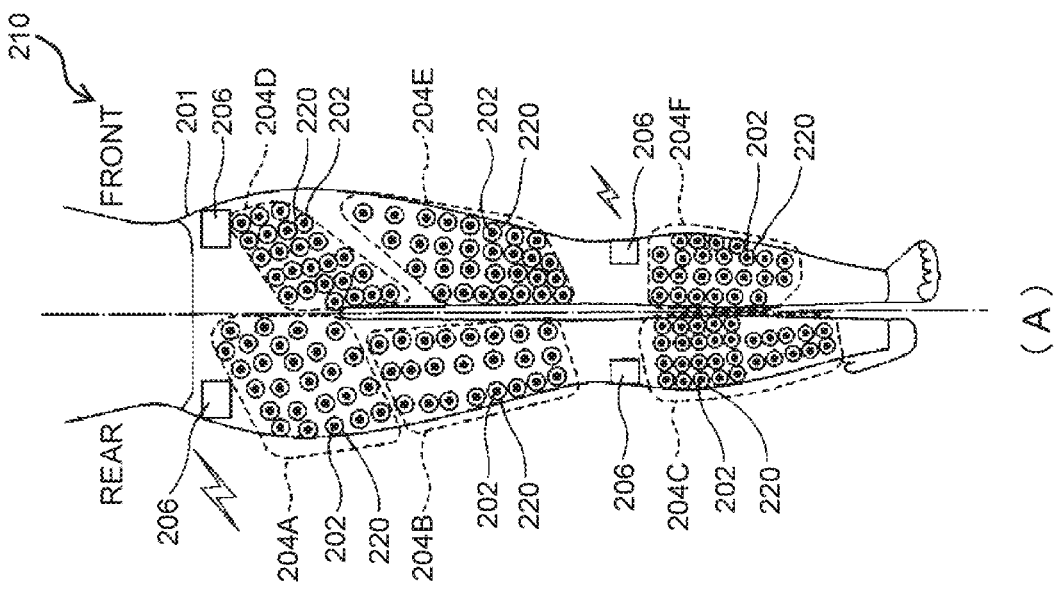
FIG. 8

BIOLOGICAL ACTIVITY DETECTION APPARATUS AND BIOLOGICAL ACTIVITY DETECTION SYSTEM

CROSS-REFERENCE TO RELATED APPLICATIONS

This application is a U.S. National Stage entry of PCT Application No: PCT/JP2017/030393 filed Aug. 24, 2017, which claims priority to Japanese Patent Application No. 2016-164009, filed Aug. 24, 2016, the contents of which are incorporated herein by reference.

TECHNICAL FIELD

The present invention relates to a biological activity detection apparatus and a biological activity detection system and is particularly suited for use in a biological activity detection apparatus and biological activity detection system for presenting transmission routes of a cranial nervous system and an activity status of a musculoskeletal system as visualized information.

BACKGROUND ART

In recent years, development of various power assistance apparatuses for assisting or substituting motions of a subject who has motor functional disorder has been being promoted. As an example of these power assistance apparatuses, a wearable motion assistance apparatus capable of controlling and assisting physical activities based on a bioelectric potential associated with voluntary muscle activities according to the subject's intention has been in widespread use.

Such a wearable motion assistance apparatus not only performs the motion assistance according to the subject's intention, but also can be applied to, for example, rehabilitation for the purpose of recovery of the motor function.

Under such circumstances, it is desirable if a linked state of a body's nervous systems can be visualized and evaluated in order to diagnose the subject's motor function; however, for example, Magnetic Resonance Imaging (MRI) can discriminate the central nerves among nerve tissues by viewing images, but under the present circumstances it is difficult to further discriminate peripheral nerves by viewing images.

In recent years, there have been proposed many methods for imparting stimuli to specified sites of the subject's nervous system model or dermatome and recognizing the connection state of nerve areas and how they are linked based on nerve responses to such stimuli.

For example, there is proposed a method for identifying abnormalities of ganglions by acquiring a map model of an autonomic nervous system and dominant nerve data related to parameter settings together with a ganglion indicator from the subject and analyzing that map model and set parameters (see PTL 1).

There is also proposed a method of mounting an electrode array, which can apply stimuli and detect the results, on the subject and comparing and improving the measurement results of nerve responses with a body perception map (therapeutic map) which is made of a therapeutic relation between a control variable and a feedback variable (see PTL 2).

Furthermore, there is also proposed a method of generating functional images of the subject's spinal nerve structure via X-rays, associating the respective parts of the images with a plurality of nervous functions (dermatomes), and detecting electrodes for detecting a sensory nerve signal and finding a detected site and its spinal cord level (see PTL 3).

Furthermore, there is also proposed a method of imparting pulses to induce reflex reactions from a desired nerve-stimulated site in the subject' autonomic nervous system, making adjustments to cause a specified parameter to be focused on desired neural connections, and receiving feedback (see PTL 4).

CITATION LIST

Patent Literature

PTL 1: Japanese Unexamined Patent Application Publication (Translation of PCT Application) No. 2016-513526
PTL 2: Japanese Unexamined Patent Application Publication (Translation of PCT Application) No. 2014-523261
PTL 3: Japanese Patent No. 5830090
PTL 4: Japanese Patent No. 5060304

SUMMARY OF THE INVENTION

Problems to be Solved by the Invention

Meanwhile, the treatment planning method based on the analysis results of the subject's autonomic nervous system model as in PTL 1 can only recognize abnormalities in dynamic responses of, for example, organs affected by innervation; and, therefore, the above-described treatment planning method is not sufficient for practical use because it can only judge the relation with the autonomic nervous system.

Moreover, PTL 2 merely controls optimum nerve stimuli by causing the measurement results of the nerve responses to the stimuli to the subject to be fed back. Furthermore, PTL 3 is just the plan programming for electric stimuli to the spinal cord. Furthermore, regarding PTL 4, the means for constructing a closed-loop nerve stimulus system which monitors and records neural connection data merely controls a nerve stimulus signal.

Accordingly, there have been proposed many methods for imparting stimuli to the subject's body surface and recognizing the connection status of the nerve areas and how they are linked to each other based on the nerve responses to the stimuli; however, under the present circumstances, such methods have not yet accomplished checking of inherent functions of a human being including not only the cranial nervous system, but also the musculoskeletal system.

The present invention was devised in consideration of the above-described circumstances and aims at proposing a biological activity detection apparatus and biological activity detection system capable of quantitatively digitalize an activity status of the musculoskeletal system and a transmission status of the cranial nervous system by performing basic body motions, and making use of the digitalized data for medical diagnosis and treatment methods.

Means to Solve the Problems

In order to solve the above-described problems, the present invention includes: a drive unit that actively or passively drives in conjunction with a limb motion of a subject; a periarticular detection unit that detects a periarticular physical quantity around a joint in association with the limb motion of the subject on the basis of an output signal from the drive unit; a biological signal detection unit that is located at a body surface site of the subject with reference to the joint and includes an electrode group for detecting a biological signal of the subject; a biological signal processing unit that acquires a myogenic potential signal associated with muscle activities of the subject and a neural transmission signal to cause a motion of a musculoskeletal system of the subject from the biological signal acquired by the biological signal detection unit; and a status quantification unit that converts an activity status of the musculoskeletal system and/or a transmission status of a peripheral nervous system around the joint into quantitative musculoskeletal system data and/or nervous system data on the basis of either one or both of the physical quantity acquired from the periarticular detection unit and the myogenic potential signal and the neural transmission signal which are acquired from the biological signal processing unit.

As a result, as the subject performs the limb motion, the activity status of the musculoskeletal system and the transmission status of the peripheral nervous system can be quantitatively digitalized and the status of progress and the transition state of that subject can be monitored on the basis of the periarticular physical quantity and the biological signal which can be acquired from the body surface site with reference to the joint.

Moreover, a motion measurement unit that measures the limb motion of the subject directly from the limb itself or indirectly from outside is further included according to the present invention; and the periarticular detection unit detects the periarticular physical quantity in association with the limb motion of the subject together with or instead of the output signal from the drive unit.

Accordingly, diversity in detecting the periarticular physical quantity is provided by enabling measurement of the subject's limb motion not only when the subject wears the motion measurement unit directly on their body, for example, on their external skeleton, but also when the motion measurement unit is set separately from the subject's body.

Furthermore, according to the present invention, the electrode group of the biological signal detection unit is located at a desired site other than the site with reference to the joint at the body surface site of the subject; wherein the biological signal processing unit acquires the neural transmission signal to cause the motion of the musculoskeletal system of the subject from the biological signal acquired from the biological signal detection unit; and the status quantification unit converts the transmission status of either one or both of the central nervous system and the peripheral nervous system around the desired site into the quantitative nervous system data on the basis of the neural transmission signal acquired from the biological signal detection unit.

Accordingly, the biological signal is acquired from the body surface site other than the site with reference to the subject's joint, so that not only the peripheral nervous system around the joint, but also the transmission status of the central nervous system and the peripheral nervous system from the desired site can be also quantitatively digitalized and the status of progress and the transition state of that subject can be monitored.

Furthermore, a brain activity measurement unit that is mounted on a head of the subject and measures a brain wave and a cerebral blood flow in a measured area of the head is further included according to the present invention; and the status quantification unit also adds the transmission status of the central nervous system around the head based on measurement data of the brain wave and the cerebral blood flow, which is acquired from the brain activity measurement unit, as the nervous system data. Accordingly, the transmission status of the central nervous system from the subject's brain can be also quantitatively digitalized and the status of progress and the transition state of that subject can be monitored.

Further included according to the present invention are: a voluntary control unit that generates a command signal for causing the drive unit to generate motive power according to an intention of the subject based on the biological signal acquired from the biological signal detection unit; and a driving current generation unit that generates an electric current according to each corresponding biological signal based on the command signal generated by the voluntary control unit and supplies the generated electric current to the drive unit, wherein the status quantification unit also reflects a driving state of the drive unit in the musculoskeletal system data and/or the nervous system data.

Accordingly, as the drive unit applies the driving force for assisting the subject's voluntary motion and the driving state of the drive unit is also reflected in the musculoskeletal system data and the nervous system data, it makes it possible to quantitatively evaluate, based on this reflected result, to what extent the voluntary control will influence the activity status of the musculoskeletal system and the connection status of the central nervous system and the peripheral nervous system of the subject.

Furthermore, further included according to the present invention are: a gravity center detecting unit that detects a gravity center position of the subject; and a walking state recognition unit that recognizes a walking state of the subject on the bases of the driving state of the drive unit and the gravity center position detected by the gravity center detecting unit, wherein the status quantification unit also reflects a recognition result of the subject's walking state, which is acquired from the walking state recognition unit, in the musculoskeletal system data and/or the nervous system data.

Accordingly, by also causing the driving state of the drive unit, which assists the subject's voluntary motion, and the walking state based on the subject's gravity center position to be reflected in the musculoskeletal system data and the nervous system data, it makes it possible to quantitatively evaluate, based on this reflected result, to what extent the walking state by the voluntary control will influence the activity status of the musculoskeletal system and the connection status of the central nervous system and the peripheral nervous system of the subject.

Further included according to the present invention are: a stimulus imparting unit that is located corresponding to the electrode group of the biological signal detection unit and includes terminal groups to impart physical stimuli to a body surface of the subject; and a stimulus control unit that controls each of the terminal groups of the stimulus imparting unit, wherein the status quantification unit also reflects a stimuli-imparted result by the stimulus imparting unit in either one or both of the musculoskeletal system data and the nervous system data.

When there is a site where it is difficult to acquire the biological signal over the subject' body surface, physical stimuli are applied to the site and feedback learning is thereby promoted and the motor function is reconstructed and, at the same time, the stimuli-imparted result is also reflected in the musculoskeletal system data and the nervous system data, so that it makes it possible to quantitatively evaluate, based on this reflected result, to what extent the stimuli-imparted result will influence the activity status of the musculoskeletal system and the connection status of the central nervous system and the peripheral nervous system of the subject.

Furthermore, according to the present invention, the stimulus control unit adjusts at least one or more of a strength level, pattern, and time of the stimuli imparted by the stimulus imparting unit until any change in a signal waveform of the biological signal detected by the biological signal detection unit appears. As a result, the stimuli can be imparted in an optimum condition while adjusting the subject's constitution and health condition along a time course.

Further included according to the present invention is a map image generation unit that generates a two-dimensional or three-dimensional body map image that represents at least one or more of the activity status of the musculoskeletal system and the transmission status of the central nervous system and the peripheral nervous system on the basis of either one or both of the musculoskeletal system data and the nervous system data. Accordingly, the activity status of the musculoskeletal system and the transmission status of the central nervous system and the peripheral nervous system can be visualized as body map images and the status can be easily visually checked.

Further included according to the present invention is a physiological information detection unit that detects physiological information of the subject, wherein the status quantification unit also reflects the physiological information, which is acquired from the physiological information detection unit, in the musculoskeletal system data and/or the nervous system data. It makes it possible to quantitatively evaluate, based on this reflected result, to what extent the physiological information will influence the activity status of the musculoskeletal system and the connection status of the central nervous system and the peripheral nervous system of the subject.

Further included according to the present invention is a living information detection unit that detects living information representing daily behaviors of the subject, wherein the status quantification unit also reflects the living information, which is acquired from the living information detection unit, in the musculoskeletal system data and/or the nervous system data. It makes it possible to quantitatively evaluate, based on this reflected result, to what extent the living information will influence the activity status of the musculoskeletal system and the connection status of the central nervous system and the peripheral nervous system of the subject.

Further included according to the present invention is an appearance acquisition information detection unit that detects appearance acquisition information representing a body reaction of the subject, wherein the status quantification unit also reflects the appearance acquisition information, which is acquired from the appearance acquisition information detection unit, in the musculoskeletal system data and/or the nervous system data. It makes it possible to quantitatively evaluate, based on this reflected result, to what extent the appearance acquisition information will influence the activity status of the musculoskeletal system and the connection status of the central nervous system and the peripheral nervous system of the subject.

Further included according to the present invention are: the biological activity detection apparatus; a signal processing unit that is provided in the biological activity detection apparatus, acquires the musculoskeletal system data and/or the nervous system data from the status quantification unit, and transmits the musculoskeletal system data and/or the nervous system data; and a data terminal device that is provided separately from the biological activity detection apparatus, receives the musculoskeletal system data and/or the nervous system data which are transmitted from the signal processing unit, and transmits the musculoskeletal system data and/or the nervous system data to a management server via a communication line.

As a result, the musculoskeletal system data and the nervous system data which are acquired by the biological activity detection apparatus can be stored and managed in the management server, while monitoring the subject's status of progress and the transition state and utilizing the monitored results for medical diagnosis and treatment methods as necessary.

Furthermore, according to the present invention, the signal processing unit acquires diagnosis information based on the musculoskeletal system data and/or the nervous system data which are read from the management server via the data terminal device; and wherein the status quantification unit also reflects the diagnosis information in either one or both of the musculoskeletal system data and the nervous system data. It makes it possible to quantitatively evaluate, based on this reflected result, to what extent the diagnosis information will influence the activity status of the musculoskeletal system and the connection status of the central nervous system and the peripheral nervous system of the subject.

Advantageous Effects of the Invention

The present invention can implement a biological activity detection apparatus and biological activity detection system capable of quantitatively digitalizing the activity status of the musculoskeletal system and the transmission status of the central nervous system and the peripheral nervous system of a subject, acquiring such digitalized data, monitoring the status of progress and transition state of that subject, and making use of such monitoring results for the medical diagnosis and the treatment method.

BRIEF DESCRIPTION OF DRAWINGS

FIG. 6 illustrates a schematic configuration diagram and an explanatory diagram of a cerebrovascular characteristic measurement apparatus according to the present invention;

FIG. 8 illustrates an example of a biological signal measurement mounting tool for a lower body (both legs) and a measurement module according to the present invention.

DESCRIPTION OF EMBODIMENTS

An embodiment of the present invention will be described below in detail with reference to the drawings.

(1) Operation Principles of The Present Invention

When a human tries to move their body, their intention to move is transmitted as a feeble ion current to their brain, spinal cord, motor nerves, and muscles and finally the musculoskeletal system moves. A wearable motion assistance apparatus which is a patent invention of, for example, U.S. Pat. No. 4,200,492 by the inventor of this application is known.

This wearable motion assistance apparatus processes this feeble bioelectric potential information and sensor information which is incorporated into the apparatus (ground reaction force, joint angles, and acceleration information) and assists the body motions by generating necessary motor torque to assist the body motions on a real-time basis according to their intention to move.

Since the wearable motion assistance apparatus is in close contact with the body, the wearable motion assistance apparatus is driven and the mounted sites such as legs are moved according to the subject's intention, so that an Ia afferent neuron signals at muscle spindles will return to the brain through the motor nerves and the spinal cord.

Figure 1:
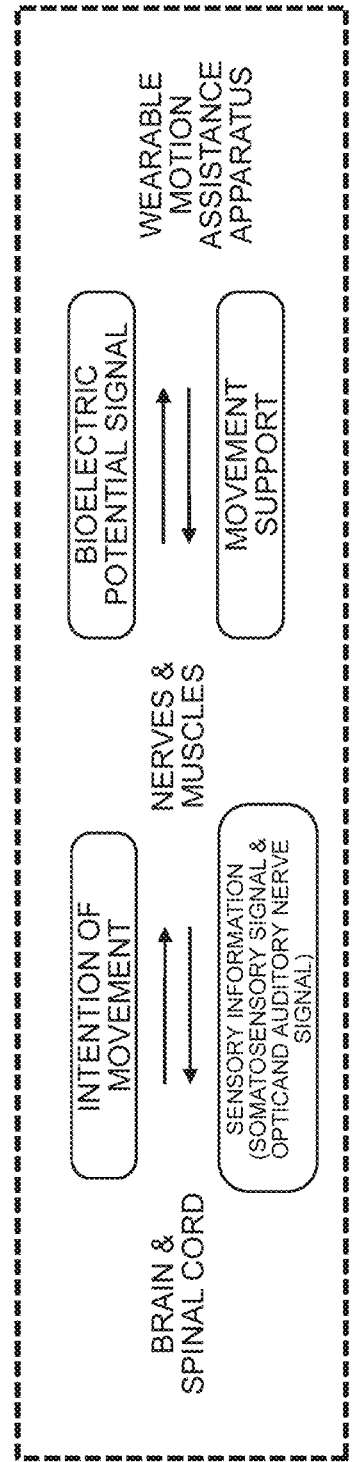
FIG. 1 is a conceptual diagram for explaining bidirectional biofeedback according to an embodiment of the present invention.

Accordingly, it has been confirmed by experiments that, as illustrated in FIG. 1, bidirectional feedback is promoted in the subject between the cranial nervous system, the body, and the wearable motion assistance apparatus, that is, from the brain sequentially through the spinal cord, the motor nerves, and the musculoskeletal system and then to the wearable motion assistance apparatus and subsequently from the wearable motion assistance apparatus, then sequentially through the musculoskeletal system, the motor nerves, and the spinal cord and then to the brain.

Moreover, when the subject has severe motor functional disorder, particularly in a state where a bioelectric potential signal has not been detected yet from the subject's body surface, autonomous control works to move like a robot by means of a program prepared based on analysis results of human basic motion patterns and motion mechanism.

It is desirable that voluntary control be performed by using the wearable motion assistance apparatus with the subject's generated muscular strength and physical stimuli be imparted as necessary so as to recognize to what level (a degree of damage) the relevant reaction area has reached in the central nervous system and the peripheral nervous system. Particularly, if recovery effects of the motor center system (the brain) and the peripheral system (the spinal cord) can be digitized by the stimuli-imparting feedback learning, the risk of the motor functional disorder can be avoided or reduced.

The present invention generates quantitative musculoskeletal system data which represent the activity status of the musculoskeletal system depending a detected position of the bioelectric potential and quantitative nervous system data which represent neural transmission routes of the central system and/or the peripheral system, while supplementarily applying motive power according to the bioelectric potential detected from the subject's body surface to the subject's joint motions in accordance with the subject's intention.

Specifically speaking, the present invention is designed so that as the subject only performs the limb motion(s), the activity status of the musculoskeletal system and the transmission status of the peripheral nervous system are quantitatively digitalized based on the periarticular physical quantity and the biological signal which can be acquired from the body surface site with reference to the joint.

Incidentally, examples of the periarticular physical quantity according to the present invention include identification of at least one or more parameters among the generated muscular strength which is generated at skeletal muscles, a variable area, variable speed, and reaction rate of each joint, autonomous control characteristics against disturbances, the moment of inertia, mass, and the center of gravity of the frames, impedance (viscosity characteristics by frictions) of the articular system including flexor muscles and extensor muscles, and electrical physical quantity (command signals).

Moreover, the biological signal according to the present invention is a signal attributable to electricity generated within the subject's body, a signal which can be measured, and also a signal which changes in chronological order in association with motions of the body and signals from the brain. For example, the biological signal means electric potential generated by biochemical reactions such as neural electric potential, myogenic potential, brain waves, cardiac potential, and also electric potential generated by motion artifacts (influences of motions) and signals generated by activities of a living body such as vibrations of pulse waves caused by heartbeats. The generated electric potential (amplitude, density, and time delay) of the biological signal and the generated site are also added to quantitative digitalization.

Moreover, the subject's head is also a target to acquire the bioelectric potential and measurement results of brain waves and cerebral blood flows in a measured area of the head are added as nervous system data which is the transmission status of the central nervous system.

By accumulating and managing the musculoskeletal system data and the nervous system data for each subject via a communication line in an external management server, it makes it possible to contribute to medical diagnosis and searches for treatment methods from the transition state along with subsequent time course. If mapping processing is executed on the musculoskeletal system data and the nervous system data to generate two-dimensional or three-dimensional body map images, the activity status of the musculoskeletal system and the transmission status of the nervous system can be visualized.

Furthermore, a driving state of the relevant drive unit is also reflected in the musculoskeletal system data and the nervous system data by transmitting motive power according to the subject's intention as a command signal to the drive unit. When the subject's lower limbs are set as detection targets, a recognized result of the subject's walking state is also reflected in the musculoskeletal system data and the nervous system data.

Furthermore, recovery of the nerves can be ensured and also changes in the neural transmission route can be visualized by imparting physical stimuli to the subject's body surface site and promoting recovery of the state of perception from biological tissues of that site.

Furthermore, state transitions of the neural transmission route of the cranial nervous system can be visualized by associating the respective changes in the subject's physiological information (such as blood pressure, arteriosclerosis, electrocardiograph, breathing, swallowing, and sleeping), living information (a fall history, a vital state by sounds, a behavior history, an eating and drinking history, and a bathing state by sounds), and appearance acquisition information (such as eye motions, body temperature distribution, body motion reactions with respect to a visual sense state and an auditory sense state, facial expressions, and leg-lifting motions) with levels of nervous activity electric potential and reflecting the results in map data.

Incidentally, the musculoskeletal system data and the nervous system data which are accumulated in the management server can be utilized as diagnosis information for medical diagnosis and treatment methods and measures. Diseases related to body motions and physical activities and physiological diseases fall under the diagnosis information and dementia-related information is further included in the diagnosis information.

(2) Biological Activity Detection System According to This Embodiment

An explanation will be provided regarding an embodiment of a biological activity detection system to which a wearable motion assistance apparatus for the full body is applied as a biological activity detection apparatus for quantitatively digitalizing the activity status of the musculoskeletal system and the transmission status of the peripheral nervous system according to the present invention and which manages musculoskeletal system data and nervous system data acquired from the wearable motion assistance apparatus.

Figure 2:
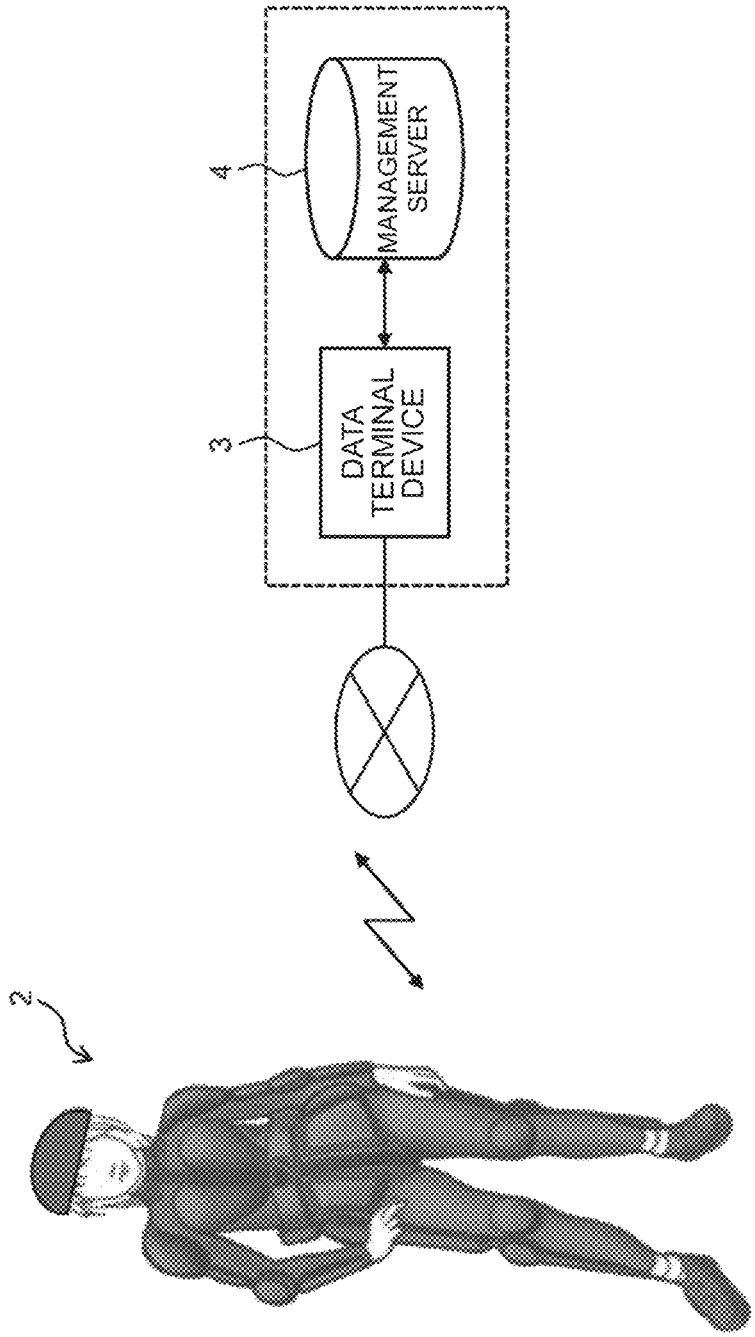
FIG. 2 is a schematic diagram illustrating an overall configuration of a biological activity detection system according to an embodiment of the present invention.

Referring to FIG. 2, a biological activity detection system 1 is configured so as to include a systemic wearable motion assistance apparatus 2, a data terminal device 3, and a management server (accumulated database) 4.

The wearable motion assistance apparatus 2 illustrated in FIG. 2 is equipped with the respective driving units such as shoulder joint mechanisms, elbow joint mechanisms, a joint mechanism in the crotch, and knee joint mechanisms, and a signal processing unit (which is not shown in the drawing) for wirelessly transmitting the musculoskeletal system data and the nervous system data which are quantitatively acquired based on various kinds of sensors and the like for detecting brain activity information, physiological information, living information, and appearance acquisition information.

This signal processing unit is used to transmit the musculoskeletal system data and the nervous system data via the signal processing unit over a communication network on a regular basis or irregularly according to, for example, a specific instruction operation. The data terminal device 3 receives the musculoskeletal system data and the nervous system data transmitted over the communication network and the management server 4 can collectively manage the musculoskeletal system data and the nervous system data.

(3) Biological Activity Detection Apparatus According to This Embodiment (3-1) Configuration of Wearable Motion Assistance Apparatus (Hardware for Lower Body)

Figure 3:
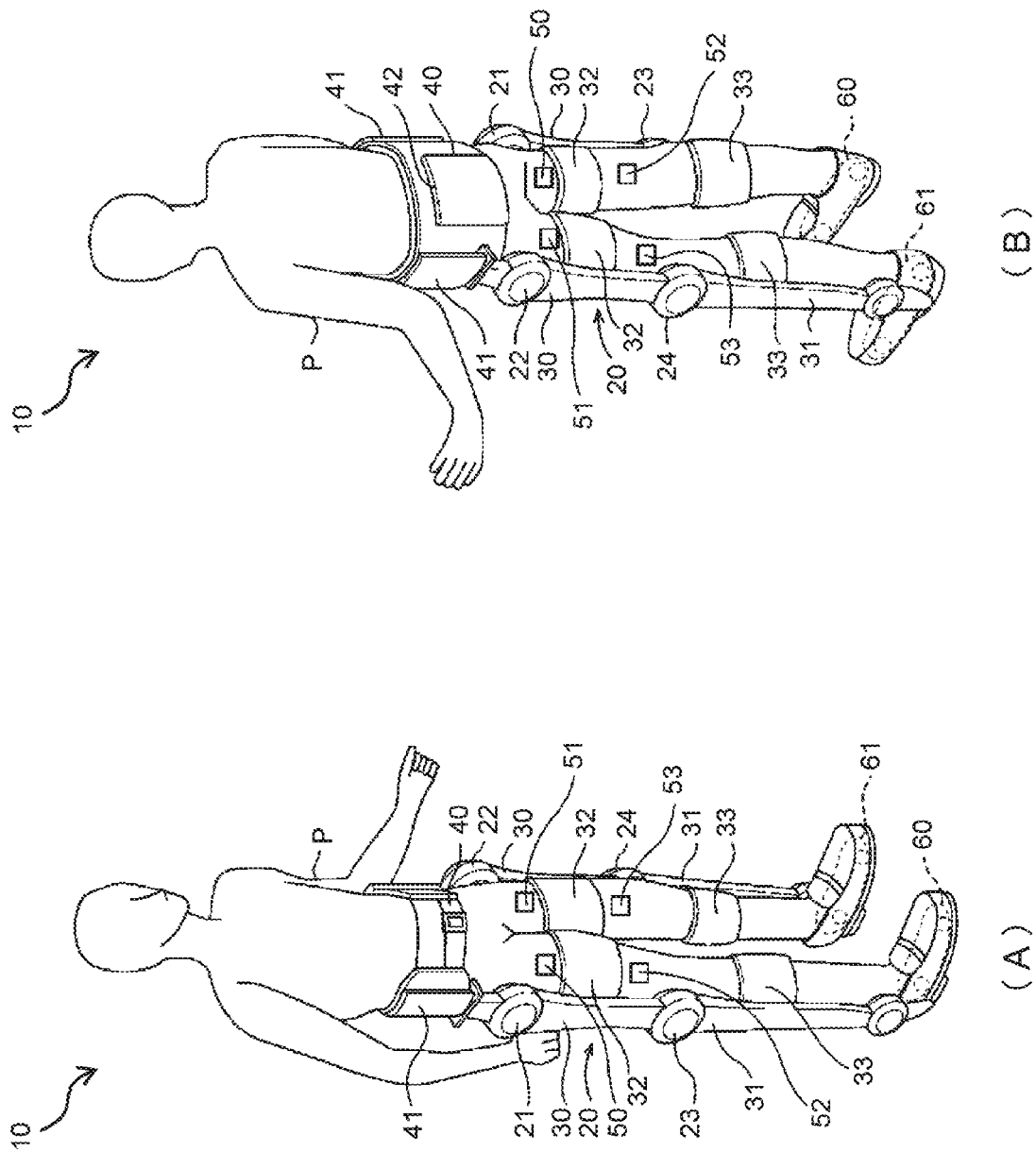
FIG. 3 is an external view illustrating the configuration of a wearable motion assistance apparatus according to an embodiment of the present invention.

An explanation will be provided regarding a case where a wearable motion assistance apparatus 10 for the lower body according to this embodiment is applied as the biological activity detection apparatus. FIG. 3 is a diagram illustrating an example of a state where the subject is wearing the wearable motion assistance apparatus 10. The wearable motion assistance apparatus 10 is designed so that, for example, frames which are mounted along areas between joints of a human body (the subject's body) such as the lower back, thighs, and shins are coupled to actuator units in a freely rotatable manner.

The wearable motion assistance apparatus illustrated in FIG. 3 is the wearable motion assistance apparatus 10 for the lower body, which includes actuator units at knee joints and hip joints; however, the wearable motion assistance apparatus 2 (FIG. 3) for the upper body or the full body can also be used according to the present invention.

The wearable motion assistance apparatus 10: detects a biological signal (for example, a signal generated from a human body such as surface myogenic potential) which is generated when causing muscle strength by means of a signal from the brain of the subject P; and operates to impart a driving force from an actuator on the basis of this detected signal.

When the subject P wearing the wearable motion assistance apparatus 10 performs a walking notion with their own intention, driving torque according to the then-generated biological signal is applied as an assist force from the wearable motion assistance apparatus. Accordingly, the subject P can walk while supporting their entire body weight with a resultant force of their own muscle strength and the driving torque from the actuator (for example, an electric drive motor).

When this happens, the wearable motion assistance apparatus 10 performs control so that the assist force (motor torque) applied according to movements of the center of gravity caused by the walking motion reflects the intention of the subject P. Therefore, the actuator of the wearable motion assistance apparatus 10 is controlled to not impose load against the intention of the subject P and to not interfere with the motions of the subject P.

Moreover, the wearable motion assistance apparatus 10 can assist motions, besides the walking motion, according to the intention of the subject P, for example, a motion of the subject P standing up from a state of being seated on a chair, a motion of sitting on a chair from a standing state, and further motions of the subject P going up or down stairs. Particularly, when the muscle strength is weak, it is difficult to perform the motion of going up the stairs or the motion of standing up from the chair; however, the subject P wearing the wearable motion assistance apparatus 10 can perform motions with the driving torque applied according to their own intention without worrying about reduction of the muscle strength.

The wearable motion assistance apparatus 10 is formed by providing a frame mechanism 20, which is to be worn by the subject P, with actuators (drive units). The actuators (drive units) include: a right-thigh driving power unit 21 positioned at a right-side hip joint of the subject P; a left-thigh driving power unit 22 positioned at a left-side hip joint of the subject P; a right-knee driving power unit 23 positioned at a right-knee joint of the subject P; and a left-knee driving power unit 24 positioned at a left-knee joint of the subject P. These driving power units 21 to 24: are drive units which are composed of servo motors whose driving torque is controlled by a control signal from a control device 80 (FIG. 4); have a speed reduction mechanism that reduces a speed of rotations of the motor at a specified speed reduction rate; and are of a small size, but can provide a sufficient driving force.

A rotation axis of the driving power unit 21 to 24 is configured so that it transmits the driving torque to first frames 30 and second frames 31, which are the driven side, via a gear mechanism. The first frames 30 are formed along the outside of thighs of the subject P and the second frames 31 extend below the first frames 30 and along the outside of shins of the subject P.

A belt-like thigh-fastening member 32 to be fastened to the thigh of the subject P is attached to an intermediate position of the first frame 30 in its longitudinal direction. A belt-like shin-fastening member 33 to be fastened to the shin under the knee of the subject P is attached to an intermediate position of the second frame 31 in its longitudinal direction. Therefore, the driving torque generated by the driving power units 21 to 24 is transmitted via gears to the first frames 30 and the second frames 31 and further transmitted as an assist force to the legs of the subject P via the thigh-fastening members 32 and the shin-fastening members 33.

A belt-like lower-back-fastening member 40 mounted on the lower back of the subject P is equipped with a rechargeable battery 41 that functions as a power source to drive the driving power units 21 to 24.

Moreover, the wearable motion assistance apparatus 10 has a controlling unit 42 to be mounted on the rear-side back of the lower-back-fastening member 40 on the back side of the subject P. This controlling unit 42 accommodates equipment such as the control device 80, a motor driver, a measurement apparatus, and a power supply circuit.

Furthermore, the wearable motion assistance apparatus 10 includes: a bioelectric potential sensor 50 that detects a biological signal (a surface myogenic potential and a nervous activity electric potential) associated with movements of the right thigh of the subject P; a bioelectric potential sensor 51 that detects a biological signal associated with movements of the left thigh of the subject P; a bioelectric potential sensor 52 that detects a biological signal associated with movements of the right knee of the subject P; and a bioelectric potential sensor 53 that detects a biological signal associated with movements of the left knee of the subject P.

Each of these bioelectric potential sensors 50 to 53: is a detection unit that measures the nervous activity electric potential which is issued from the brain towards the legs to move the legs of the subject P and the surface myogenic potential when the skeletal muscles generate the muscle strength; and has an electrode for detecting feeble electric potential generated at, for example, the skeletal muscles. Incidentally, in this embodiment, each bioelectric potential sensor 50 to 53 is attached to the surface of the subject's skin with, for example, an adhesive seal or the like to cover an area around the electrode in a freely attachable/detachable manner.

Therefore, the wearable motion assistance apparatus 10 is configured to assist the subject's walking motion with the assist force applied by calculating a driving current to be supplied to the driving power units 21 to 24 based on the biological signals detected by these bioelectric potential sensor 50 to 53 and driving the driving power units 21 to 24 with this driving current.

Moreover, it is necessary to detect a load imposed on the soles of the feet in order to cause smooth movements of the center of gravity by the walking motion. Therefore, the soles of the right and left feet of the subject P are provided with reaction force sensors 60, 61 that measure the load at at least two points on the soles of the feet. Each reaction force sensor 60, 61 is composed of, for example, piezoelectric elements for outputting a voltage according to the imposed load and can detect changes in the load as caused by movements of the body weight and whether the legs of the subject are in contact with the ground or not.

Moreover, the actuator has an angle sensor and a torque sensor built therein. For example, a torque sensor which detects a value of the electric current supplied to the driving power unit 21 to 24 and detects the driving torque by multiplying this electric current value by a torque constant specific to the actuator can be applied as this torque sensor. Moreover, for example, a rotary encoder or the like can be applied as the angle sensor.

Incidentally, the case where the reaction force sensors 60, 61 (gravity center detecting units) are applied to detect the gravity center position of the subject has been described; however, the present invention is not limited to this example and the gravity center position by the subject's walking motion may be detected according to various methods based on positional information of leg motions and joints without measuring the load on the soles of the feet.

(3-2) Control System of Wearable Motion Assistance Apparatus

The control system of the wearable motion assistance apparatus 10 according to this embodiment shares the same content with, and uses the same principles as, that described in Japanese Registered Patent No. 4178187 by the inventor of the present application.

Figure 4:
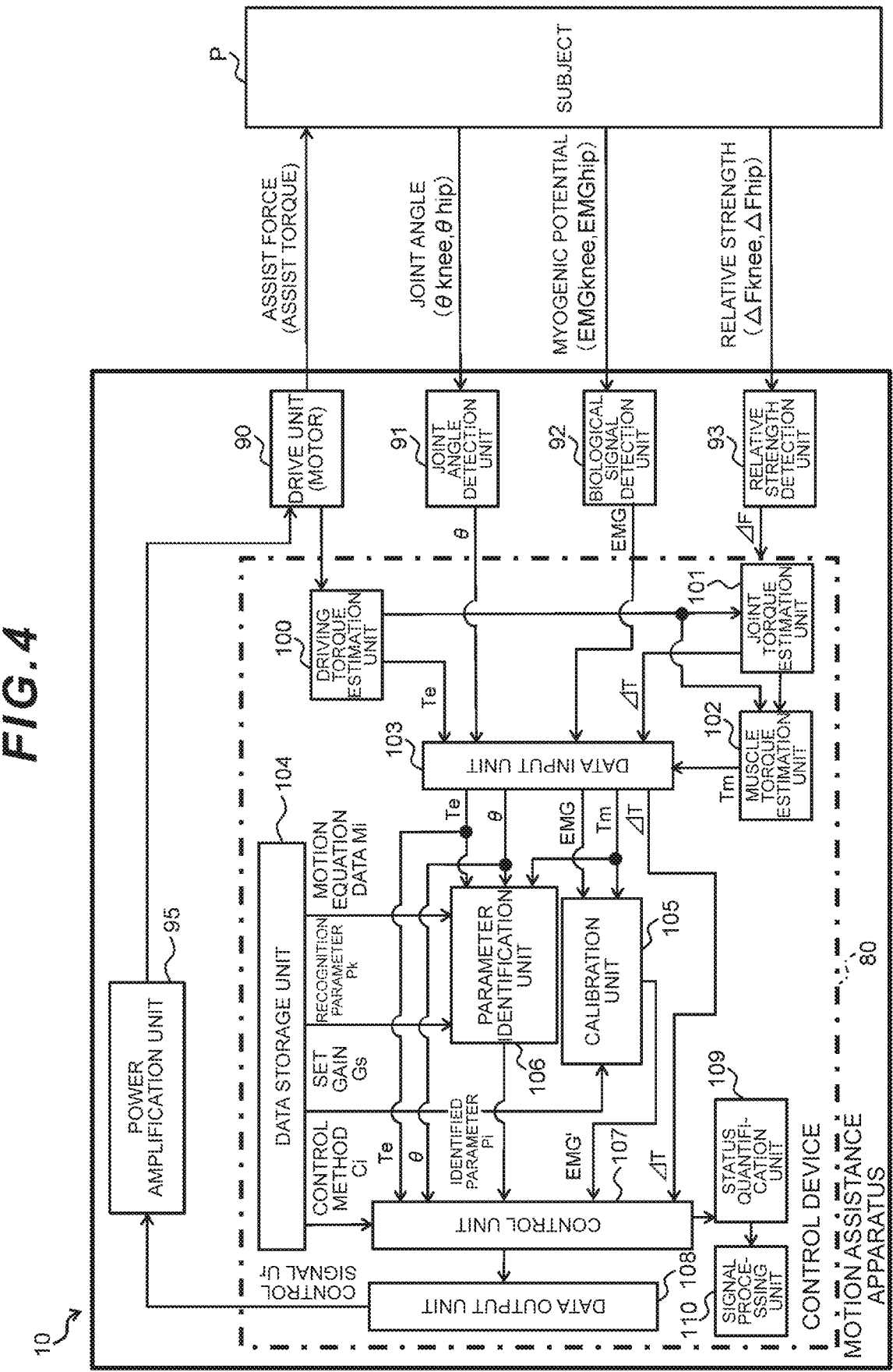
FIG. 4 is a block diagram illustrating the configuration of a control system for the wearable motion assistance apparatus according to an embodiment of the invention.

The wearable motion assistance apparatus 10 includes, as illustrated in FIG. 4, a drive unit (corresponding to the driving power units 21 to 24 in FIG. 1) 90 which applies the assist force to the subject, a joint angle detection unit 91 which detects angular displacement θ of each joint of the subject, a biological signal detection unit (corresponding to bioelectric potential sensors 50 to 53 in FIG. 1) 92 which detects the myogenic potential (biological signal) according to the generated muscle strength of the subject, and a relative strength detection unit 93 which detects relative strength (ΔF) that acts on the wearable motion assistance apparatus 10.

The assist force herein used is a force to generate torque acting with each joint of the frame mechanism 20 (corresponding to each of the subject's knee joint and hip joint) as the rotation axis. The relative strength detection unit 93 detects a force which acts on the frame mechanism 20, that is, a force relatively determined by the relation between a force generated by the drive unit 90 and the subject's muscle strength.

The wearable motion assistance apparatus 10 according to this embodiment controls the assist force by using, as the biological signal, for example, a bioelectric potential signal (BES: Bio-Electrical Signal) which is a command signal from the upper central nervous system generated in a form of electric potential on the surface of muscles via the spinal cord.

Moreover, the wearable motion assistance apparatus 10 includes a control device 80 which drives and controls the drive unit 90 through a power amplification unit 95. The control device 80 includes a driving torque estimation unit 100, a joint torque estimation unit 101, a muscle torque estimation unit 102, a data input unit 103, a data storage unit 104, a calibration unit 105, a parameter identification unit 106, a control unit 107, a data output unit 108, a status quantification unit 109, and a signal processing unit 110.

The driving torque estimation unit 100 estimates driving torque (Te) generated by the drive unit 90. For example, the driving torque estimation unit 100 which estimates the driving torque (Te) by detecting a value of the electric current supplied to the drive unit 90 and multiplying this electric current value by the torque constant which is specific to the drive unit 90 can be applied.

The joint torque estimation unit 101 estimates joint moment (ΔT) around each joint of the subject from the difference between a result obtained by multiplying the relative strength data (ΔF) detected by the relative strength detection unit 93 by a coefficient previously set and the driving torque estimation data (Te). Since the resultant force of the driving torque (Te) and the drive unit 90 and the subject's muscle torque (Tm) acts as the joint moment (ΔT) on the subject's legs, the subject can move their legs with less muscle strength than the case without wearing the frame mechanism 20.

The muscle torque estimation unit 102 estimates muscle torque (Tm) by the subject's muscle strength based on the driving torque estimation data (Te) estimated by the driving torque estimation unit 100 and the joint moment estimation data (ΔT) estimated by the joint torque estimation unit 101. Incidentally, the muscle torque (Tm) is estimated in order to enable parameter identification even under the condition where the subject generates the muscle strength; and it is advantageous to do so in a case where the parameter identification is performed when the subject is in a motion state.

The data input unit 103 is an input interface for the detected data from various kinds of detection units and the estimated data from various kinds of estimation units in the wearable motion assistance apparatus 10. The data storage unit 104 stores necessary data for the control device to execute various arithmetic processing.

The parameter identification unit 106 constructs a target motion equation in an arithmetic environment by using motion equation data (Mi) and known parameters (Pk), which are read from the data storage unit 104, and is configured so that the driving torque estimated value (Te), the joint torque estimated value (ΔT), and the joint angle θ from the data input unit 103 can be substituted in the relevant motion equation.

The motion equation data (Mi) herein used is to construct the motion equation for the entire system composed of the wearable motion assistance apparatus 10 and the subject, while the known parameters (Pk) are composed of kinetic parameters such as the weight of each unit of the wearable motion assistance apparatus 10, the moment of inertia around each joint, viscosity coefficient, and clone friction coefficient.

The parameter identification unit 106 executes the arithmetic processing by even taking the read driving torque estimation data (T'), the joint data (θ) and the joint moment data (ΔT), and also the muscle torque (Tm) into consideration, identifies unknown kinetic parameters (Pu) such as the weight of each part of the subject, the moment of inertia around each joint, viscosity coefficient, and clone friction coefficient, repeats the identification more than once (for example, 10 times) to obtain average values, and sends them to the control unit.

The calibration unit 105 reads a ratio of the estimated muscle torque (Tm) to the myogenic potential (EMG) from the data input unit 103 (Tm/EMG) and specified set gain (Gs) from the data storage unit 104; and if the set gain (Gs) is out of an allowable error range (Ea), the calibration unit 105 corrects the myogenic potential data (EMG) to obtain the corrected myogenic potential data (EMG') and makes a ratio of the muscle torque (Tm) to the corrected myogenic potential (EMG') (Tm/EMG') substantially equal to the set gain (Gs).

As a result, it is possible to prevent the situation where the accuracy for identifying the subject's unknown parameters (Pu) may degrade; and it is also possible to prevent the situation where the assist force generated by the drive unit 90 may become excessively small or large.

The control unit 107 is configured so as to be capable of reading the control method data (Ci) from the data storage unit, the driving torque estimated value (Te), the joint torque estimated value (ΔT), and the joint angle θ from the data input unit 103 as well as an identification parameter (Pi) from the parameter identification unit 106 and the corrected myogenic potential (EMG') from the calibration unit 105.

Moreover, the control unit 107 can send out a control signal Ur for driving and controlling the drive unit 90 by constructing a specified control means in the arithmetic environment by using the control method data (Ci) and reflecting the driving torque estimated value (Te), the joint torque estimated value (ΔT), the joint angle θ, the identification parameter (Pi), and the myogenic potential (EMG') in this control means.

The data output unit 108 is an output interface for sending out the control signal Ur from the control unit 107 to the power amplification unit. The power amplification unit 95 drives the drive unit 90 according to the control signal Ur from the data output unit 108.

Furthermore, the wearable motion assistance apparatus 10 is designed to control the assist force based on impedance adjustments in order to resolve interferences with natural control attributable to restrictions by physical characteristics of the apparatus itself, that is, viscoelasticity around the joints and inertia of the frames. In other words, the wearable motion assistance apparatus 10 realizes enhancement of an assist rate in the walking motion and reduction of the subject's uncomfortable feeling by calculating joint parameters and compensating for the moment of inertia, viscosity, and elasticity by means of the actuator.

With the wearable motion assistance apparatus 10 as described above, the characteristics of the subject can be indirectly changed and adjusted by changing the characteristics of the entire system which is the apparatus itself plus the subject. For example, by adjusting the driving torque so that influences by an inertia term and a viscous friction term of the entire system can be suppressed, the subject's inherent abilities to perform prompt motions such as reflexes can be exercised to a maximum extent. Furthermore, influences by the subject's own inertia term and viscous friction term can be also suppressed and the subject can be made to walk faster than their original cycle or to move more smoothly (with less viscous frictions) than before wearing the apparatus.

Furthermore, the wearable motion assistance apparatus 10 can cause the parameter identification unit 106 to identify the kinetic parameters specific to the relevant subject in a state of being mounted on the subject and cause the control device 80 to control the drive unit 90 on the basis of the motion equation in which the identified kinetic parameters are substituted, so that effects according to the control method employed by the control device 80 can be produced without depending on any variation factors such as personal differences or health condition of the subject.

Moreover, the drive unit 90 can be controlled by the control device 80 based on the motion equation in which the muscle torque (Tm) estimated by the muscle torque estimation unit 102 is also substituted. So, the kinetic parameters can be identified even in the state where the muscle strength is generated from the subject; and the above-described effects can be produced without requiring the subject to suffer waiting time to identify the kinetic parameters.

Since the calibration unit 105 which adjusts the gain between the myogenic potential (EMG) detected by the biological signal detection unit 92 and the muscle torque (Tm) detected by the muscle torque estimation unit 102 so that such gain becomes a set gain (Gs) which is previously set is further included, it is possible to prevent the situation where defective sensitivity or excessive sensitivity may occur in the detected result from the biological signal detection unit 92.

As a result, it is possible to prevent the situation where the accuracy for identifying the subject's kinetic parameters may degrade; and it is also possible to prevent the situation where the assist force generated by the drive unit 90 may become excessively small or large. What is more, the wearable motion assistance apparatus 10 according to this embodiment can perform calibration even in a state where the muscle strength is generated from the subject, and the subject is not required to suffer waiting time to perform the calibration.

Since at least either one of gravity compensation and inertia compensation using the kinetic parameters identified by the parameter identification unit 106 can be applied to the control device 80, it is possible to prevent the situation where the weight of the apparatus itself may impose a burden on the subject, and to prevent the situation where during a motion the inertia of the apparatus itself may give the subject an uncomfortable feeling.

With the control device 80, the status quantification unit 109 converts the activity status of the musculoskeletal system and the transmission status of the peripheral nervous system around the relevant joint into the quantitative musculoskeletal system data and the nervous system data on the basis of the myogenic potential signal and the neural transmission signal, which are supplied from the control unit 107, and the periarticular physical quantity.

The periarticular physical quantity includes the identification results of at least one or more parameters among the generated muscular strength produced at the skeletal muscles, the variable area, variable speed, and reaction rate of each joint, autonomous control characteristics against disturbances, the moment of inertia, mass, and center of gravity of the frames, and impedance adjustment results of the articular system including the flexor muscles and the extensor muscles (viscosity characteristics by frictions), and the electrical physical quantity (command signal).

The signal processing unit 110 has a wireless communication function and transmits the musculoskeletal system data and the nervous system data, which are supplied from control unit 107, to the data terminal device 3 via the communication network. With the data terminal device 3 as described earlier, the management server 4 collectively manages the musculoskeletal system data and the nervous system data for each subject and utilizes such data for medical care and treatment methods.

Accordingly, as the drive unit 90 provides the driving force to assist the subject's voluntary motions and the driving state of the drive unit 90 is also reflected in the musculoskeletal system data and the nervous system data, it makes it possible to quantitatively evaluate, based on the reflected result, to what extent voluntary control will influence the activity status of the musculoskeletal system and the connection status of the central nervous system and the peripheral nervous system of the subject.

(3-3) Assist Control Associated with Subject's Walking Motion

Next, an explanation will be provided regarding assist control executed by the control device 80 in association with the subject's walking motion when the wearable motion assistance apparatus is worn by the subject.

After identifying a phase of a task corresponding to the subject's motion by checking the joint angle ($\theta$) and the myogenic potential signal (EMG) against a reference parameter database (not shown in the drawing), the control unit 107 selects a command function f(t) and gain P according to the relevant phase.

When the difference $\Delta$EMG between a biological signal (EMGop) and a myogenic potential signal (EMGex) which are reference parameters corresponding to the joint angle is equal to or more than a preset allowable value (threshold value), the myogenic potential for the subject's joint motion does not correspond to the subject's motion; and, therefore, the control unit 107 changes the gain P to the corrected gain P'(<P) by an arithmetic operation of P×{1−($\Delta$EMG/EMGop)}.

As a result, the driving power units 21 to 24 (the drive unit 90) generates the driving torque based on an actual measured value of the myogenic potential signal (EMG) according to the subject's intention regardless of the phase of each motion and transmits this driving torque as the assist force via the frames to the subject's legs.

Accordingly, for example, even when the subject tries to stop a motion (phase) in the middle of the motion and shift to another motion (phase) in order to execute processing for changing the gain P, it is possible to perform the control so that the assist force will reduce and the original motion will not be forced against the subject's intention at the point where the subject's myogenic potential signal decreases. Therefore, the subject can obtain the assist force according to the subject's intention by the control method in which autonomous control and optional control close to voluntary control are combined.

Subsequently, the control unit 107 specifies the phase of the subject's motion by comparing the joint angle detected by the joint angle detection unit 91 and the load detected by the reaction force sensors 60, 61 with the joint angle and load which are reference parameters stored in the reference parameter database.

The control unit 107 generates a command signal according to control data of the specified phase and supplies a command signal for causing the drive unit 90 to generate this motive power to the power amplification unit 95. The power amplification unit 95 applies the assist force to the subject's joint by controlling the electric current to drive the actuator of the drive unit 90 and thereby control the torque size and rotation angle of the actuator.

The data storage unit 104 stores the reference parameter database for specifying the phase(s) of the subject's task(s) and assist parameters for assisting the subject's movements according to the specified phase. Tasks are classified major motion patterns of a human being. A phase is a series of minimum motion unit constituting each task.

Figure 5:
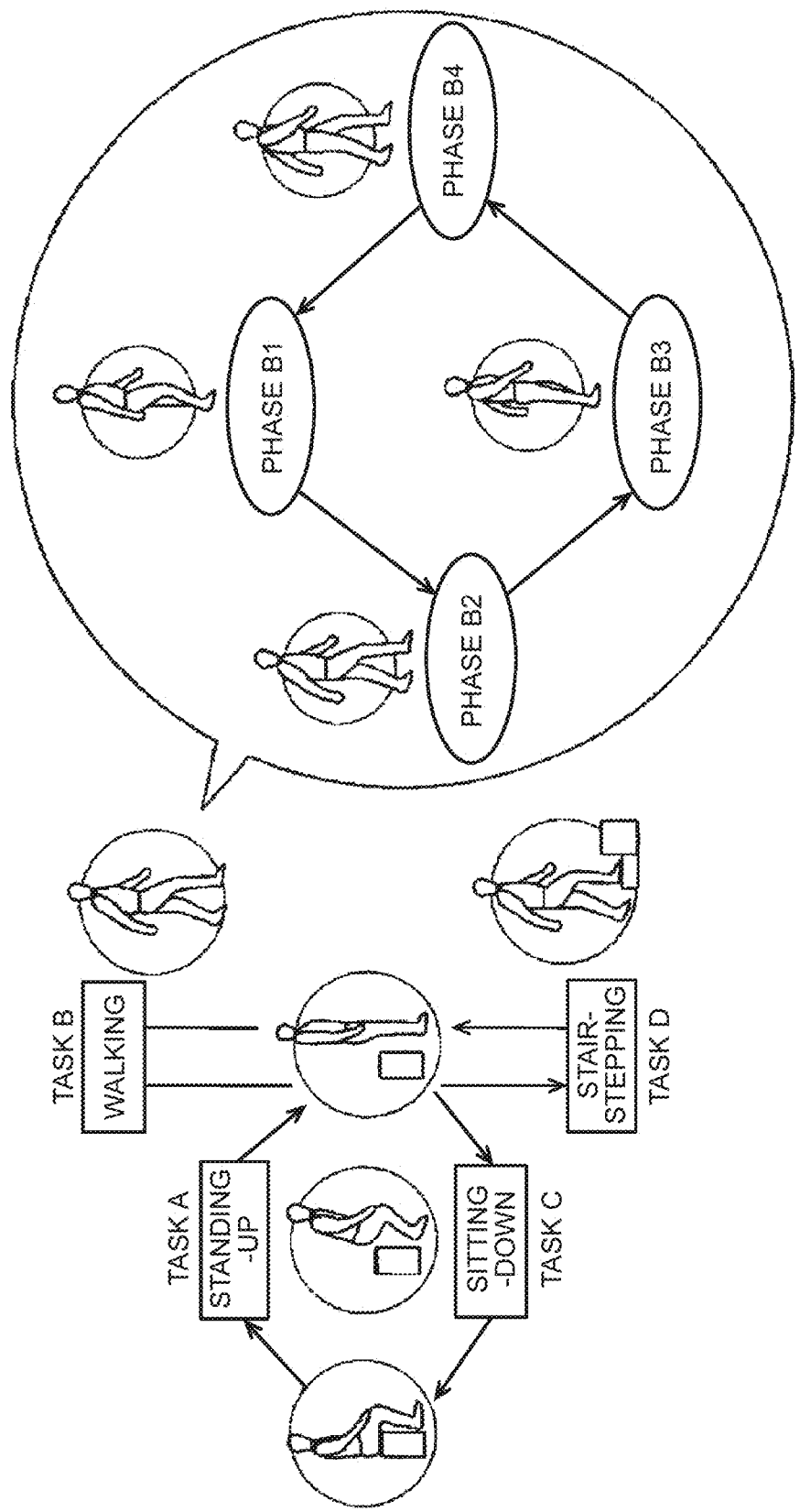
FIG. 5 is a conceptual diagram illustrating tasks which classify a subject's motions according to the embodiment.

FIG. 5 illustrates an example of the respective tasks and the respective phases which are stored in the reference parameter database. Regarding the tasks which classify the subject's motions, for example, task A with standing-up motion data to make the transition from a seated state to a standing state, task B with walking motion data for the subject P who has stood up to walk, task C with sitting-down motion data to make the transition from the standing state to the seated state, and task D with stair-stepping motion data to go up and down the stairs from the standing state are stored in the reference parameter database.

Then, a plurality of pieces of phase data are set to each task. For example, the following phases are set to task B of the walking motion: phase B with motion data (such as trajectories of the joint angle and the gravity center position, changes of the torque, and changes of the bioelectric potential signal) to swing the right leg forwards from the standing state with the center of gravity placed on the left leg; phase B with motion data from the state with the right leg placed in front to the state of landing on the ground and shifting the center of gravity; phase B with motion data to swing the left leg forwards from the standing state with the center of gravity placed on the right leg; and phase B with motion data from the state with the left leg in front of the right leg to the state of landing on the ground and shifting the center of gravity.

Accordingly, when common motions of a human being are analyzed, you can see that some typical motion patterns are determined such as the angle of each joint and movements of the center of gravity in each phase. So, typical joint angle displacement and the movement status of the center of gravity are found empirically with respect to each of the phases which constitute many basic motions (tasks) of a human being and these data are stored in the reference parameter database.

Moreover, a plurality of assistance patterns are assigned to each phase and different assists are provided even in the same phase.

Accordingly, the control device 80 includes the walking state recognition unit (the control unit 107) which recognizes the subject's walking state based on the driving state of the drive unit 90 and the subject' gravity center position; and the status quantification unit 109 also reflects the recognition results of the subject' walking state obtained from the walking state recognition unit (the control unit 107) in the musculoskeletal system data and/or the nervous system data.

Examples of the recognition results of the subject's walking state include not only walking patterns, a walking cycle, and phase information of each joint (including phase information based on the gravity center position and the joint angle), but also movements of the center of gravity and changes in the trunk's motions and interlocked motions. Incidentally, the walking state is mainly divided into a period of motion to move a leg away from the ground and swing a lower leg forwards (swing leg period) and a period where the legs are in contact with the ground and supports their own weight (stance leg period), and time switching between these periods is also included in the recognition results of the walking state.

Accordingly, by also reflecting the driving state of the drive unit which assists the subject's voluntary motions and the walking state based on the relevant subject's gravity center position in the musculoskeletal system data and the nervous system data, it makes it possible to quantitatively evaluate, based on the reflected result, to what extent the walking state by the voluntary control will influence the activity status of the musculoskeletal system and the connection status of the central nervous system and the peripheral nervous system of the subject.

(4) Cerebrovascular Property Measurement Apparatus

A cerebrovascular characteristic measurement apparatus 120 according to this embodiment shares the same content with, and uses the same principles as, that described in Japanese Registered Patent No. 5283700 by the inventor of the present application.

The cerebrovascular characteristic measurement apparatus 120 includes, as illustrated in FIG. 6A, a blood flow measurement unit 121, an electrocardiograph 122, a control unit 123, and a radio communication device 124. The blood flow measurement unit 121 measures the blood flow condition by checking changes in optical paths of a laser beam and a transmitted light volume as caused by blood flows and further measures the brain activity status from the blood flow condition in the brain.

Specifically speaking, when a laser beam applied to the blood enters a blood layer, the laser beam permeates and advances through the blood as the light of both components, that is, light components reflected and scattered by normal red blood cells and light components reflected and scattered by attached thrombi. Since the influences on the laser beam in the process of permeating through the blood layer changes every second depending on the blood condition, it is possible to observe various changes in the blood condition by continuously measuring the transmitted light volume (reflected light volume) and observing changes in that light volume.

The blood flow measurement unit 121 is composed of: a net-like base 125 which is formed in a hemispherical shape according to the external shape of a head so that it can be mounted on the head; and many sensor units 130A to 130N. Each sensor unit 130A to 130N is supported by the net-like base 125 at a specified distance between them and outputs a detection signal of the transmitted light volume which is measured at each measurement point of the head to the control unit 123.

The electrocardiograph 122 causes an electrode E which is affixed on the subject's skin to measure cardiac potential generated according to movements of the heart 129.

The control unit 123: derives changes in positions of blood vessels and tissues around the blood vessels by the blood flows on the basis of optical intensity when light 126 (FIG. 6B) emitted from a light-emitting unit of each sensor unit 130A to 130N is received by a light-receiving unit 127; and measures the activity status of the brain (distribution of red blood cells). Moreover, the control unit 123 stores a control program which executes arithmetic processing to, for example, cancel components by oxygen saturation included in the signal obtained from at least two or more light-receiving units 127.

Furthermore, the control unit 123 derives changes in positions of inner walls of the blood vessels based on the changes in the positions of the blood vessels and the tissues around the blood vessels. Furthermore, the control unit 123 finds a pulse wave velocity at each measured position from a phase difference between a waveform of an electrocardiograph signal from the electrocardiograph 122 and a waveform of a detection signal obtained from the light-receiving unit and derives the position change status of the inner walls of the blood vessels from the pulse wave velocity.

The radio communication device 124 transmits the measurement results (blood flow data), which have been output from the control unit 123, wirelessly to external equipment. Since the cerebrovascular characteristic measurement apparatus 120 has the optical sensor units 130 placed over the net-like base 125, it can measure the blood flows over the entire head at the same time.

When measuring blood vessel characteristics of the brain, as illustrated in FIG. 5B, the control unit 123 selects an arbitrary sensor unit 130D from among the multiplicity of arranged sensor units 130A to 130N and causes the light-emitting unit 126 of the sensor unit 130D to emit a laser beam. When this happens, the laser beam emitted from the light-emitting unit 126 is output with wavelength $\lambda$, ($\lambda \approx 805$ nm) which will not be affected by oxygen saturation.

When the blood flow measurement unit 121 of the cerebrovascular characteristic measurement apparatus 120 is mounted on the subject's head, the elasticity of the net-like base 125 allows the plurality of sensor units 130 to be positioned at the respective measurement points on the head and the respective measurement faces to be retained in the state of being positioned opposite the head surface. In the state where the blood flow measurement unit 121 is mounted on the head, the plurality of sensor units 130 can measure blood vessel characteristics of the middle cerebral arteries and the anterior cerebral arteries (an elasticity rate of the blood vessels, an amount of plaques in the blood vessels, and an arteriosclerosis rate) by radiating light over the surface of the brain and measuring the pulse wave velocity in cerebral arteries from changes in the received light volume of the light which propagates in the brain.

Incidentally, the principles of measuring the pulse wave velocity of the cerebral arteries will be explained. For example, the pulse wave velocity by the blood flows through the middle cerebral arteries and the anterior cerebral arteries is detected by each sensor unit placed corresponding to the measured position where the light which has propagated through the brain is received when the light is radiated. As a measurement method, there is used a method of comparing the waveform of the cardiac potential obtained from the electrocardiograph with the waveform of the signal output from each sensor unit at the measured position, finding the pulse wave velocity from the phase difference, and deriving the blood vessel characteristics corresponding to the pulse wave velocity.

Moreover, the principles of the case where the blood vessel characteristics are detected from the blood flows in the brain will be explained. As illustrated in FIG. 6B, a brain 150 is covered with a cerebrospinal fluid 151, a skull 152, and a scalp 153. Regarding the laser beam emitted from the light-emitting unit 126 of each sensor unit 130 for the blood flow measurement unit 121, part of the light reflects off the scalp 153, while the remaining light permeates through the scalp 153, the skull 152, and the cerebrospinal fluid 151 and advances inside the brain 150. Then, the light which has advanced into the brain, of the light radiated over the head, propagates in radiation directions (in a depth direction and a radial direction) with circular patterns 160 as illustrated with broken lines in the drawing.

As the light which permeates through the brain propagates farther away from a base point 161, on which the laser beam was radiated, in its radial direction, a light propagation path becomes longer and light transmittance decreases. Consequently, a light-receiving level (transmitted light volume) of the sensor unit 130B, which is adjacent to the sensor unit 130A on the light-emitting side and with a specified distance separated from the sensor unit 130A, is detected as being strong. Then, the light-receiving level (transmitted light volume) of the sensor unit 130C, which is provided adjacent to the sensor unit 130B and with a specified distance separated from the sensor unit 130B, is detected as being weaker than the light-receiving level of the sensor unit 130B. Moreover, even the light-receiving unit 127 of the sensor unit 130A on the light-emitting side receives the light from the brain 150.

The control unit 123 derives the blood vessel characteristics of each measured position by using the detection signal according to optical intensity of the light received by the plurality of sensor units 130 as measurement data and comparing the waveform of the detection signal with the waveform of the cardiac potential signal from the electrocardiograph 122. Moreover, graphic data representing a distribution of arteriosclerosis according to the pulse wave velocity can be obtained by executing mapping processing on the above-described detection results.

Therefore, by using the waveform of the detection signal of each sensor unit 130A to 130N, changes in the blood flows through the middle cerebral arteries and the anterior cerebral arteries can be measured and the pulse wave velocity in the brain 150 can be detected from the measurement data of the blood flow changes.

Accordingly, the cerebrovascular characteristic measurement apparatus 120 includes the brain activity measurement unit (the blood flow measurement unit 121) which is mounted on the subject' head and measures the brain wave and the cerebral blood flow in the measured areas of the head; and the status quantification unit 109 (FIG. 4) is designed to also add the transmission status of the central nervous system around the head based on the measurement data of the brain wave and the cerebral blood flow, which are obtained from the brain activity measurement unit (the blood flow measurement unit 121), as the nervous system data. Consequently, the transmission status of the central nervous system from the subject's brain can also be quantitatively digitalized and acquired and the status of progress and the transition state of the subject can be monitored.

(5) Biological Signal Measurement Mounting Tool

A biological signal measurement mounting tool 200 according to this embodiment shares the same content with, and uses the same principles as, that described in Japanese Registered Patent No. 5409637 by the inventor of the present application.

Figure 7:
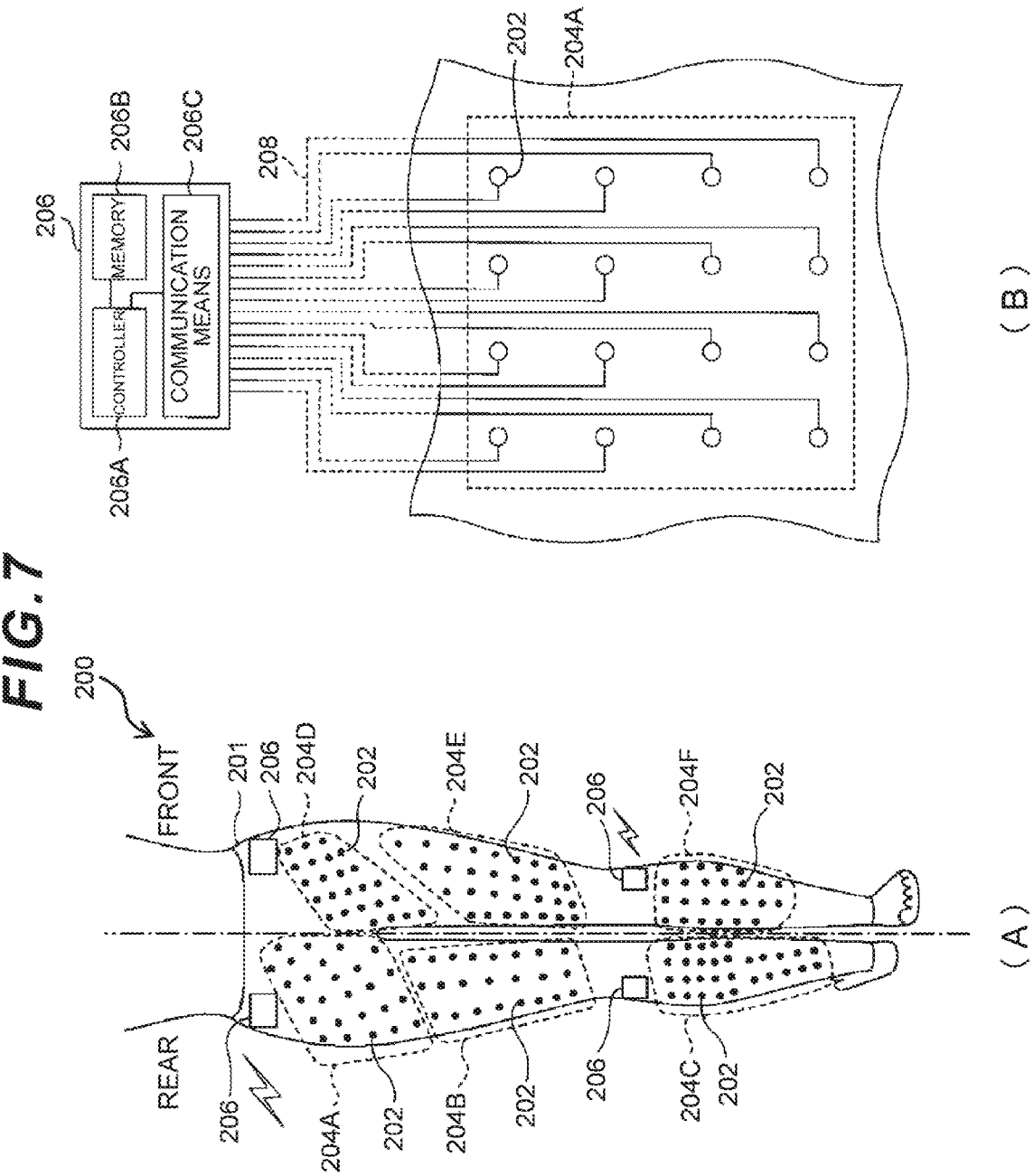
FIG. 7 illustrates an example of a biological signal measurement mounting tool for a lower body (both legs) and a measurement module according to the present invention.

FIG. 7A illustrates the biological signal measurement mounting tool 200 according to this embodiment. This biological signal measurement mounting tool 200 is formed to cover the subject's body surface and includes a mounting tool body 201 to be mounted on the subject; and an inner surface of this mounting tool body 201 (a surface to be in contact with the subject' body surface in the mounted state) includes a biological signal sensor(s) 202 for detecting a bioelectric potential signal at at least one position where a biological signal from the subject can be measured.

Since the biological signal measurement mounting tool 200 according to this embodiment has a bilaterally symmetric structure, the left half part of FIG. 7A illustrates the structure of a rear side of a left leg and the right half part of FIG. 7A illustrates the structure of a front side of the left leg. The mounting tool body 201 is provided with biological signal sensor groups 204A to 204F composed of a plurality of biological signal sensors 202 for detecting the subject's biological signal. The biological signal sensors 202 are arranged at regular intervals along flows of muscles of the subject's legs.

The mounting tool body 201 has the plurality of biological signal sensors 202 arranged in a part corresponding to the subject's hips (the biological signal sensor group 204A) along the flow of a gluteus maximus muscle. And similarly, the mounting tool body 201 has the plurality of biological signal sensors 202 arranged: in a part corresponding to the rear side of the subject's femur (the biological signal sensor group 204B) along the flow of a biceps femoris muscle, a semimembranosus muscle, and a semitendinosus muscle; and in a part corresponding to the calf (the biological signal sensor group 204C) along the flow of a triceps surae muscle. Moreover, the mounting tool body 201 has the plurality of biological signal sensors 202 arranged: in a site corresponding to the front side of the hip joint (the biological signal sensor group 204D) along the flow of a long adductor muscle and a liopsoas muscle; in a site corresponding to the front side of the femur (the biological signal sensor group 204E) along the flow of a quadriceps femoris muscle; and in a site corresponding to the shin (the biological signal sensor group 204F) along the flow of a tibialis anterior muscle, a soleus muscle, and an extensor digitorum longus muscle.

Now, FIG. 7B is a diagram illustrating an example of a measurement module (biological signal acquisition unit) coupled to the biological signal sensor group 204A mounted in the mounting tool body 201. Incidentally, since all the biological signal sensor groups 204A to 204F provided in the mounting tool body are coupled to the measurement module in the same manner, an explanation will be provided here by taking the biological signal sensor group 204A as an example.

FIG. 7B is a diagram schematically illustrating the biological signal sensor group 204A provided in the mounting tool body 201 and a measurement module 206 coupled to this biological signal sensor group 204A. The respective biological signal sensors 202 constituting the biological signal sensor group 204A are provided in a state of being isolated from each other and are coupled to the measurement module 206 via conductive wiring. Then, an address is assigned to each of these biological signal sensors 202.

The measurement module 206: is coupled to the plurality of biological signal sensors 202 which constitute the biological signal sensor group 204A; and includes a measurement module controller 206A which selects at least two biological signal sensors 202 from these biological signal sensors 202 and acquires a biological signal by finding a difference between detection signals detected by these selected biological signal sensors 202, a memory 206B which records the acquired biological signals, and a communication unit 206C which externally transmits the sequentially acquired biological signals and/or the biological signals recorded in the memory 206B. Incidentally, the measurement module 206 is provided for each biological signal sensor group 204A to 204F and each biological signal sensor 202 is coupled to the relevant measurement module 206.

This measurement module controller 206A includes an electronic circuit capable of sequentially selecting at least two biological signal sensors 202 from the plurality of coupled biological signal sensors 202 according to a command signal which is input via the communication unit 206C and acquiring a biological signal between these two selected biological signal sensors 202.

Moreover, the measurement module controller 206A further includes signal processing means such as a filter for eliminating or removing a specified frequency component from the thus-acquired biological signal and an amplifier for amplifying the acquired biological signal. The thus-acquired biological signal is output from the measurement module controller 206A to the communication unit 206C and/or the memory 206B. When the measurement module controller 206A selects the biological signal sensors 202, it may sequentially operate the respective biological signal sensors 202 in a preset order or may select a biological signal sensor 202 with the address designated by a designation signal which is input via the communication unit 206C.

The communication unit 206C is composed of a thin antenna and a communication circuit coupled to this antenna. The communication unit 206C transmits measurement information which includes a signal including the biological signal output from the measurement module controller 206A and information such as the address representing positional information of the biological signal sensor 202 which detected the relevant biological signal, and/or a signal including the biological signal read from the memory 206B and information such as the address representing positional information of the biological signal sensor 202 which detected the relevant biological signal, via the antenna to the control device 80 (FIG. 3).

The control unit 107 for this control device 80 generates, for example, the designation signal to designate which biological signal sensor 202 to be selected from the respective biological signal sensor groups 204A to 204F provided in the mounting tool body 201 and signals to start and terminate the acquisition of data and transmits these signals to the control device 80 via the antenna. The control device 80 selects the designated biological signal sensor 202 according to the received signals and measures the biological signal.

Accordingly, regarding the biological signal measurement mounting tool 200 according to the present invention, the mounting tool body 201 is equipped with the biological signal sensor groups 204A to 204F composed of the plurality of biological signal sensors 202, so that the plurality of biological signal sensors 202 can be located at specified sites at once and be made to be in close contact with the skin surface to detect the biological signal at each point simply by wearing the mounting tool body 201. Consequently, also when monitoring the biological signals at many points on the subject's body surface, it is possible to save the trouble of affixing or removing the biological signal sensors 202 one by one and easily measure the biological signals.

Moreover, the biological signals can be measured at a plurality of respective points in the areas where the biological signal sensor groups 204A to 204F are located, by causing the plurality of biological signal sensors 202 to detect the biological signals as described above. Then, a distribution of the biological signals in the subject's body can be measured by mapping the measurement data at each point according to the address assigned to each biological signal sensor 202.

(6) Biological Signal Measurement Mounting Tool (Imparting of Biological Stimuli)

A biological signal measurement mounting tool 210 according to this embodiment shares the same content with, and uses the same principles as, that described in Japanese Patent Application Laid-Open (Kokai) Publication No. 2013-179966 by the inventor of the present application.

Referring to FIG. 8A and FIG. 8B in which the same reference numerals as those in FIG. 7A and FIG. 7B are indicated and assigned to parts corresponding to those in FIG. 7A and FIG. 7B, a plurality of sets of a biological stimulus imparting unit 220 with contact parts 220A, which are to be in contact with the subject's body surface and apply physical (mechanical, electrical, and/or thermal) stimuli according to a biological stimulus signal, and the biological signal sensors 202 described earlier in FIG. 6 are located in a matrix form on the mounting tool body 201 for the biological signal measurement mounting tool 210.

Incidentally, the biological stimulus imparting unit 220 in FIG. 8B has a stimulus information display unit 220B which displays information according to a physical stimulus condition. An example of the stimulus information display unit 220B is an LED element whose brightness changes according to the biological stimulus signal. Accordingly, the level of the stimulus applied by the biological stimulus imparting unit 220 can be visually observed from outside.

The control unit 107 (stimulus control unit) for the control device 80 (FIG. 4) uses the biological stimulus signal to cause the contact part 220A for the biological stimulus imparting unit 220 to operate and generates the next biological stimulus signal based on a signal output by the biological signal detection unit 92 according to a signal output from the subject as caused by the above-described operation.

Incidentally, the control unit 107 (stimulus control unit) for the control device 80 (FIG. 3) may adjust at least one or more of a strength level, pattern, and time of stimulus imparted by the biological stimulus imparting unit 220 until any change in a signal waveform of the biological signal detected from the biological signal detection unit 92 appears.

When there is a site where it is difficult to acquire the biological signal over the subject' body surface, physical stimuli are applied to the site and feedback learning is thereby promoted and the motor function is reconstructed and, at the same time, the stimuli-imparted result is also reflected in the musculoskeletal system data and the nervous system data, so that it makes it possible to quantitatively evaluate, based on this reflected result, to what extent the stimuli-imparted result will influence the activity status of the musculoskeletal system and the connection status of the central nervous system and the peripheral nervous system of the subject.

(7) Advantageous Effects of This Embodiment

According to this embodiment as described above, as the subject performs a limb motion by using the wearable motion assistance apparatus 2, 10 for the lower limbs or the full body, the biological activity detection system 1 can monitor the status of progress and the transition state of the relevant subject by converting the activity status of the musculoskeletal system and the transmission status of the peripheral nervous system into the quantitative musculoskeletal system data and the nervous system data on the basis of the periarticular physical quantity and the biological signal, which can be acquired from the body surface site with reference to the joint, and accumulating such data in the management server 4.

Then, as a result of monitoring the musculoskeletal system data and the nervous system data, which are accumulated in the management server 4, for a medium and long term, treatment control can be systematized by classifying subject groups on a disease name basis (such as cerebral apoplexy, neurological disorders like spinal cord injuries, and intractable neurological and muscular diseases) and constructing and implementing verification protocols with the cooperation by the subjects and conducting analysis by clinical demonstration tests in order to enable the treatment control for each of the above-mentioned disorders and diseases.

As a result of this, the systematization of the treatment control and the construction of clinical trial protocols can be realized; and furthermore, interactive biofeedback inside the human body is promoted by using a method of assisting motions with the biological signals which reflect the intention of the motions, so that it makes it possible to verify hypotheses to promote functional improvements in the central system and the peripheral system of neurological and muscular disease patients, the number of whom increases as people age.

(7) Reflection of Various Kinds of Information Acquired from Subject (7-1) Reflection of Physiological Information Incidentally, in this embodiment, the wearable motion assistance apparatus 10 may include a physiological information detection unit (which is not shown in the drawing) for detecting the subject's physiological information; and the status quantification unit 109 (FIG. 4) may also reflect the physiological information, which is obtained from the physiological information detection unit, in the musculoskeletal system data and/or the nervous system data in the signal processing unit 110.

Examples of the physiological information include the subject's vital signs such as blood pressure, electrocardiograph, heart rate, breathing rate, body temperature, urination and defecation condition, brain waves, and consciousness level, as well as arteriosclerosis degree, arterial blood oxygen saturation (SpO2), swallowing, and sleeping. Furthermore, a blood pressure reaction rate of the heart according to the subject's activity status may also be included as the physiological information. Then, for example, a sensor or measurement apparatus for acquiring the corresponding physiological information is applied to the physiological information detection unit.

It makes it possible to quantitatively evaluate to what extent the physiological information will influence the activity status of the musculoskeletal system and the connection status of the central nervous system and the peripheral nervous system of the subject, on the basis of the result of reflecting such physiological information in the musculoskeletal system data and/or the nervous system data.

(7-2) Reflection of Living Information

Moreover, in this embodiment, the wearable motion assistance apparatus 10 may include a living information detection unit (which is not shown in the drawing) for detecting living information which represents the subject's daily behaviors; and the status quantification unit 109 (FIG. 4) may also reflect the living information, which is obtained from the living information detection unit, in the musculoskeletal system data and/or the nervous system data in the signal processing unit 110.

Examples of the living information include a vital state by the subject's spoken voices (the relation between moods and their changes and the content of speeches by language information) and the subject's fallen state, moving state, behavior state, eating and drinking state, and bathing state (voice information). Then, for example, a sensor or measurement apparatus for acquiring the corresponding physiological information is applied to the physiological information detection unit.

It makes it possible to quantitatively evaluate to what extent the physiological information will influence the activity status of the musculoskeletal system and the connection status of the central nervous system and the peripheral nervous system of the subject, on the basis of the result of reflecting such physiological information in the musculoskeletal system data and/or the nervous system data.

(7-3) Reflection of Appearance Acquisition Information

Furthermore, in this embodiment, an appearance acquisition information detection unit (which is not shown in the drawing) for detecting appearance acquisition information representing the subject's body reactions may be included; and the status quantification unit 109 (FIG. 4) may also reflect the appearance acquisition information, which is obtained from the appearance acquisition information detection unit, in the musculoskeletal system data and/or the nervous system data in the signal processing unit 110.

Examples of the appearance acquisition information include the subject's eye motions, pupillary reflexes, a distribution of body temperatures, body motion reactions to a visual sense state and an auditory sense state, facial expressions, and a degree of leg lifting (a degree of thigh lifting). Then, for example, an imaging camera, a vision sensor, thermosensitive sensor, or measurement apparatus for acquiring the corresponding appearance acquisition information detection unit is applied to the appearance acquisition information detection unit.

It makes it possible to quantitatively evaluate to what extent the appearance acquisition information will influence the activity status of the musculoskeletal system and the connection status of the central nervous system and the peripheral nervous system of the subject, on the basis of the result of reflecting such appearance acquisition information in the musculoskeletal system data and/or the nervous system data.

(8) Other Embodiments

The aforementioned embodiment has described the case where the wearable motion assistance apparatus 2, 10 is applied so that the subject wears the frame mechanism unit 20, the drive unit 90, and so on on their lower limbs or their full body; however, the present invention is not limited to this example and a motion measurement unit (which is not shown in the drawing) which measures the subject's limb motion directly from the relevant limbs themselves or indirectly from outside may be included.

Specifically speaking, a motion support apparatus which operates to support physical activity patterns of the upper limbs and the lower limbs of the subject in a state of lying in a bed or in a state of being seated on a chair, and a vison sensor or acceleration sensor which measures the subject's limbs indirectly from outside can be applied as the motion measurement unit which measures the limb motions other than the drive unit 90. In this case, the periarticular detection unit (the joint angle detection unit 91) may detect the periarticular physical quantity associated with the subject's limb motion together with or instead of the output signal from the drive unit 90.

Accordingly, diversity in detecting the periarticular physical quantity can be provided by enabling measurement of the subject's limb motion not only when the subject wears the motion measurement unit directly on their body, for example, on their external skeleton, but also when the motion measurement unit is set separately from the subject's body.

Moreover, this embodiment has described the case where the biological signal measurement mounting tool 200 (FIG. 7) is applied to the wearable motion assistance apparatus 10 for the lower limb and the electrode groups (the biological signal sensors 202) of the biological signal detection unit 92 (the biological signal sensor groups 204A to 204F) are located around periarticular areas in the subject's lower limbs; however, the present invention is not limited to this example and such electrode groups may be located freely at desired sites of the subject's body surface sites.

Figure 9:
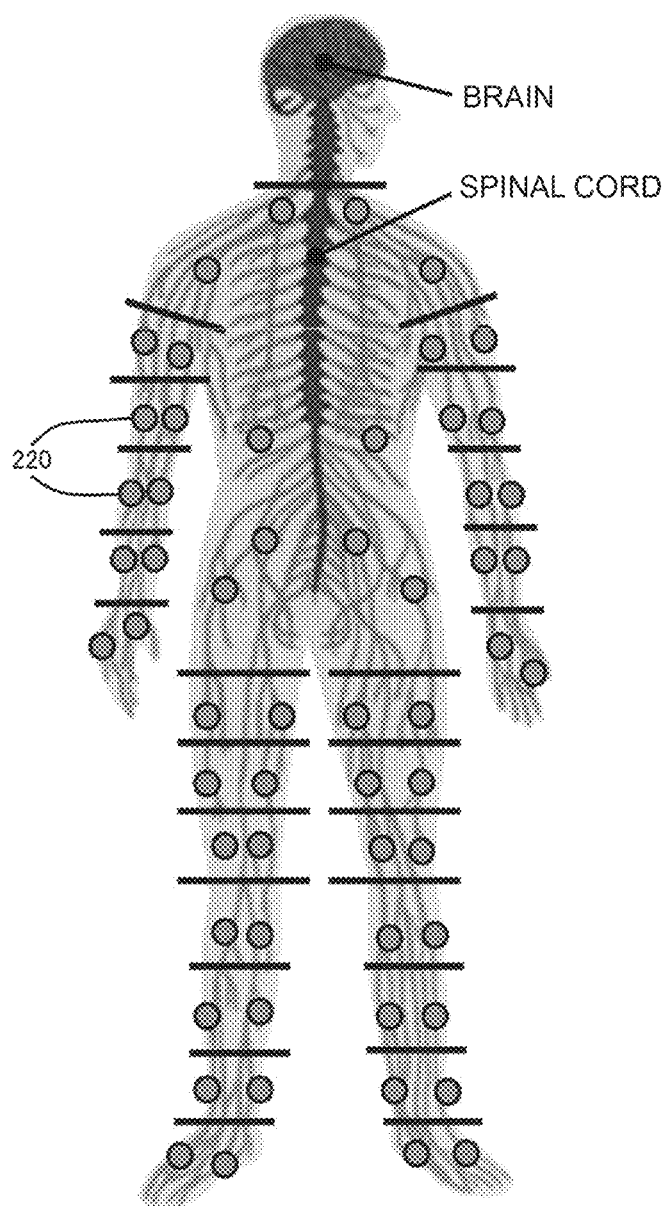
FIG. 9 is a schematic diagram for explaining state transition of cranial nervous system information transmission routes according to an embodiment of the present invention.

For example, as illustrated in FIG. 9, the state transition of information transmission routes in the cranial nervous system can be visualized by locating the biological signal sensor groups 202 in the subject's entire body. Referring to FIG. 9, if the subject's full body is divided into units of a specified area (for example, an area governed by sensory nerves such as a dermatome), linkage of the nerves in the entire body can be recognized from a higher perspective viewpoint and for each area site. Therefore, if at which site a failure in the neural transmission has occurred can be detected, it is possible to recognize not only that failure site, but also the degree of influence on the central side and the peripheral side.

The biological signal processing unit (the control unit 107) acquires a neural transmission signal to move the subject's musculoskeletal system from the biological signal acquired from the biological signal detection unit 92; and the status quantification unit 109 converts the transmission status of either one or both of the central nervous system and the peripheral nervous system around a desired site into the quantitative nervous system data on the basis of the neural transmission signal, thereby making it possible to also quantitatively digitalize the transmission status of the central nervous system and the peripheral nervous system from a desired body surface site and monitor the status of progress and the transition state of the relevant subject.

Furthermore, this embodiment has described the case where the biological signal measurement mounting tool 210 (FIG. 8) is applied to the wearable motion assistance apparatus 10 for the lower limb, the biological stimulus imparting units 220 with the terminal groups for imparting physical stimuli to the subject's body surface are used, and the status quantification unit 109 (FIG. 4) also reflects the stimuli-imparted result by the biological stimulus imparting unit 220 in either one or both of the musculoskeletal system data and the nervous system data; however, the present invention is not limited to this example and at least one or more of the strength level, pattern, and time of the stimuli imparted by the biological stimulus imparting unit 220 may be adjusted until any change in a signal waveform of the biological signal detected by the biological signal detection unit appears.

As a result of this, the stimuli can be applied in an optimum condition while adjusting the subject's constitution and health condition in accordance with time course; and feedback learning is thereby promoted and the motor function is reconstructed and, at the same time, the stimuli-imparted result is also reflected in the musculoskeletal system data and the nervous system data, so that it makes it possible to quantitatively evaluate, based on this reflected result, to what extent the stimuli-imparted result will influence the activity status of the musculoskeletal system and the connection status of the central nervous system and the peripheral nervous system of the subject.

Furthermore, this embodiment has described the case where the signal processing unit 110 externally transmits the musculoskeletal system data and/or the nervous system data which are converted by the status quantification unit 109 (FIG. 4) for the wearable motion assistance apparatus (the biological activity detection apparatus) 2, 10; however, the present invention is not limited to this example and there may be further included a map image generation unit (which is not shown in the drawing) which generates a two-dimensional or three-dimensional body map image representing at least one or more of the activity status of the musculoskeletal system, the transmission status of the central nervous system and the peripheral nervous system on the basis of either one or both of the musculoskeletal system data and the nervous system data. Accordingly, the activity status of the musculoskeletal system and the transmission status of the central nervous system and the peripheral nervous system can be visualized as a body map image (for example, FIG. 9) and the status can be easily visually observed.

Furthermore, this embodiment has described the case where the musculoskeletal system data and/or the nervous system data are received by the data terminal device 3 (FIG. 1) via wireless transmission from the signal processing unit 110 (FIG. 4) of the wearable motion assistance apparatus (the biological activity detection apparatus) 2, 10 and transmitted via the communication line to the management server 4; however, the present invention is not limited to this example and the wearable motion assistance apparatus (the biological activity detection apparatus) 2, 10 and the data terminal device 3 may transmit/receive data via a wired circuit.

This management server 4 may generate diagnosis information based on the musculoskeletal system data and/or the nervous system data for each subject and the data terminal device 3 may transmit the diagnosis information, which has been received from the management server 4, via a wireless circuit or a wired circuit to the signal processing unit 110 for the wearable motion assistance apparatus (the biological activity detection apparatus) 2, 10.

Examples of the diagnosis information include physical diseases (condition linked to motions and physical activities), physiological diseases, and dementia assessment which are predicted based on the musculoskeletal system data and/or the nervous system data, as well as diagnosis results by doctors who diagnosed the subject.

It makes it possible to quantitatively evaluate to which extent the diagnosis information will influence the activity status of the musculoskeletal system and the connection status of the central nervous system and the peripheral nervous system of the subject, on the basis of the result of reflecting, as feedback, such diagnosis information in the musculoskeletal system data and/or the nervous system data.

REFERENCE SIGNS LIST

1 biological activity detection system
2, 10 wearable motion assistance apparatus
3 data terminal device
4 management server
20 frame mechanism
21 to 24 driving power units
42 controlling unit
50 to 53 bioelectric potential sensors
60, 61 reaction force sensors
80 control device
90 drive unit
91 joint angle detection unit
92 biological signal detection unit
93 relative strength detection unit
95 power amplification unit
100 driving torque estimation unit
101 joint torque estimation unit
102 muscle torque estimation unit
103 data input unit
104 data storage unit
105 calibration unit
106 parameter identification unit
107, 123 control unit
108 data output unit
109 status quantification unit
110 signal processing unit
120 cerebrovascular characteristic measurement apparatus
121 blood flow measurement unit
122 electrocardiograph
200, 210 biological signal measurement mounting tool
220 biological stimulus imparting unit

The invention claimed is:

1. A biological activity detection apparatus comprising:
a periarticular detection unit that detects a periarticular physical quantity around a joint in association with a limb motion of a subject on a basis of an output signal from a drive unit that actively drives or is passively driven in conjunction with the limb motion of the subject;
a biological signal detection unit that is located at a body surface site of the subject with reference to the joint and includes an electrode group for detecting a biological signal of the subject;
a biological signal processing unit that acquires a myogenic potential signal associated with muscle activities of the subject and a neural transmission signal to cause a motion of a musculoskeletal system of the subject from the biological signal acquired by the biological signal detection unit;
a brain activity measurement unit that is mounted on a head of the subject and measures a brain wave and a cerebral blood flow in a measured area of the head; and
a status quantification unit that converts an activity status of the musculoskeletal system and/or a transmission status of a peripheral nervous system around the joint into quantitative musculoskeletal system data and/or nervous system data and converts a transmission status of a central nervous system around the head based on measurement data of the brain wave and the cerebral blood flow, which are acquired from the brain activity measurement unit, into quantitative nervous system data on the basis of either one or both of the physical quantity acquired from the periarticular detection unit and the myogenic potential signal and the neural transmission signal which are acquired from the biological signal processing unit;
a gravity center position detecting unit that detects a gravity center position of the subject; and
a walking state recognition unit that recognizes a walking state of the subject on the basis of the driving state of the drive unit and the gravity center position detected by the gravity center position detecting unit,
wherein the status quantification unit also reflects a recognition result of the subject's walking state, which is acquired from the walking state recognition unit, in the musculoskeletal system data and/or the nervous system data;
a stimulus imparting unit that is located corresponding to the electrode group of the biological signal detection unit and includes terminal groups to impart physical stimuli to a body surface of the subject;
a stimulus control unit that controls each of the terminal groups of the stimulus imparting unit,
wherein the stimulus control unit adjusts at least one or more of a strength level, a pattern, and a time of the stimuli imparted by the stimulus imparting unit until any change in a signal waveform of the biological signal detected by the biological signal detection unit appears, and
wherein the status quantification unit also reflects a stimuli-imparted result by the stimulus imparting unit in either one or both of the musculoskeletal system data and the nervous system data; and
a processor that generates a three-dimensional body map image that represents the activity status of the musculoskeletal system, the transmission status of the central nervous system, and the peripheral nervous system on the basis of either one or both of the musculoskeletal system data and the nervous system data,
wherein the processor detects appearance acquisition information representing a body reaction of the subject,
wherein the status quantification unit reflects the appearance acquisition information, which is acquired from the processor, in the musculoskeletal system data and the nervous system data, and wherein the appearance acquisition information include eye motions of the subject, pupillary reflexes, a distribution of body temperatures, body motion reactions to a visual sense state, and an auditory sense state, facial expressions, and a degree of leg lifting.

2. The biological activity detection apparatus according to claim 1, wherein the processor measures the limb motion of the subject directly from the limb itself or indirectly from outside, and wherein the periarticular detection unit detects the periarticular physical quantity in association with the limb motion of the subject together with or instead of the output signal from the drive unit.

3. The biological activity detection apparatus according to claim 1, wherein the processor is configured to generate a command signal for causing the drive unit to generate motive power according to an intention of the subject based on the biological signal acquired from the biological signal detection unit, wherein the processor is configured to generate an electric current according to each corresponding biological signal based on the command signal and supplies the generated electric current to the drive unit, and wherein the status quantification unit also reflects a driving state of the drive unit in the musculoskeletal system data and/or the nervous system data.

4. The biological activity detection apparatus according to claim 1, wherein the processor detects physiological information of the subject, and wherein the status quantification unit also reflects the physiological information, which is acquired from the physiological information detection unit, in the musculoskeletal system data and/or the nervous system data.

5. The biological activity detection apparatus according to claim 1, wherein the processor detects living information representing daily behaviors of the subject, and wherein the status quantification unit also reflects the living information, which is acquired from the processor, in the musculoskeletal system data and/or the nervous system data.

6. A biological activity detection system comprising:

the biological activity detection apparatus stated according to claim 1;

a signal processing unit that is provided in the biological activity detection apparatus, acquires the musculoskeletal system data and/or the nervous system data from the status quantification unit, and transmits the musculoskeletal system data and/or the nervous system data; and a data terminal device that is provided separately from the biological activity detection apparatus, receives the musculoskeletal system data and/or the nervous system data which are transmitted from the signal processing unit, and transmits the musculoskeletal system data and/or the nervous system data to a management server via a communication line, wherein the signal processing unit acquires diagnosis information based on the musculoskeletal system data and/or the nervous system data which are read from the management server via the data terminal device, and wherein the status quantification unit also reflects the diagnosis information in either one or both of the musculoskeletal system data and the nervous system data.

7. The biological activity detection apparatus according to claim 1, wherein the status quantification unit converts the activity status of the musculoskeletal system into the quantitative musculoskeletal system data.

8. The biological activity detection apparatus according to claim 1, wherein the status quantification unit converts the activity status of the musculoskeletal system into the nervous system data.

9. The biological activity detection apparatus according to claim 1, wherein the status quantification unit converts the activity status of the musculoskeletal system into the quantitative musculoskeletal system data and the nervous system data.

10. The biological activity detection apparatus according to claim 1, wherein the status quantification unit converts the transmission status of the peripheral nervous system around the joint into the quantitative musculoskeletal system data.

11. The biological activity detection apparatus according to claim 1, wherein the status quantification unit converts the transmission status of the peripheral nervous system around the joint into the nervous system data.

12. The biological activity detection apparatus according to claim 1, wherein the status quantification unit converts the transmission status of the peripheral nervous system around the joint into the quantitative musculoskeletal system data and the nervous system data.

13. The biological activity detection apparatus according to claim 1, wherein the status quantification unit converts the transmission status of the central nervous system into the quantitative nervous system data on the basis of the physical quantity acquired from the periarticular detection unit.

14. The biological activity detection apparatus according to claim 1, wherein the status quantification unit converts the transmission status of the central nervous system into the quantitative nervous system data on the basis of the myogenic potential signal.

15. The biological activity detection apparatus according to claim 1, wherein the status quantification unit converts the transmission status of the central nervous system into the quantitative nervous system data on the basis of the physical quantity acquired from the periarticular detection unit and the myogenic potential signal.

16. A biological activity detection apparatus comprising:

a periarticular detection unit that detects a periarticular physical quantity around a joint in association with a limb motion of a subject on a basis of an output signal from a drive unit that actively drives or is passively driven in conjunction with the limb motion of the subject;

a biological signal detection unit that is located at each of a body surface site of the subject with reference to the joint and a desired site other than the body surface site with reference to the joint and includes an electrode group for detecting a biological signal of the subject;

a biological signal processing unit that acquires a myogenic potential signal associated with muscle activities of the subject and a neural transmission signal to cause a motion of a musculoskeletal system of the subject from the biological signal acquired by the biological signal detection unit; and a status quantification unit that converts an activity status of the musculoskeletal system and/or a transmission status of a peripheral nervous system around the joint into quantitative musculoskeletal system data and/or nervous system data and converts a transmission status of either one or both of a central nervous system and the peripheral nervous system around the desired site into quantitative nervous system data on the basis of either one or both of the physical quantity acquired from the periarticular detection unit and the myogenic potential signal, and the neural transmission signal which are acquired from the biological signal processing unit;

a gravity center position detecting unit that detects a gravity center position of the subject; and a walking state recognition unit that recognizes a walking state of the subject on the basis of the driving state of the drive unit and the gravity center position detected by the gravity center position detecting unit, wherein the status quantification unit also reflects a recognition result of the subject's walking state, which is acquired from the walking state recognition unit, in the musculoskeletal system data and/or the nervous system data;

a stimulus imparting unit that is located corresponding to the electrode group of the biological signal detection unit and includes terminal groups to impart physical stimuli to a body surface of the subject;

a stimulus control unit that controls each of the terminal groups of the stimulus imparting unit wherein the stimulus control unit adjusts at least one or more of a strength level, a pattern, and a time of the stimuli imparted by the stimulus imparting unit until any change in a signal waveform of the biological signal detected by the biological signal detection unit appears, and wherein the status quantification unit also reflects a stimuli-imparted result by the stimulus imparting unit in either one or both of the musculoskeletal system data and the nervous system data; and a processor that generates a three-dimensional body map image that represents the activity status of the musculoskeletal system, the transmission status of the central nervous system, and the peripheral nervous system on the basis of either one or both of the musculoskeletal system data and the nervous system data, wherein the processor detects appearance acquisition information representing a body reaction of the subject, wherein the status quantification unit reflects the appearance acquisition information, which is acquired from the processor, in the musculoskeletal system data and the nervous system data, and wherein the appearance acquisition information include eye motions of the subject, pupillary reflexes, a distribution of body temperatures, body motion reactions to a visual sense state, and an auditory sense state, facial expressions, and a degree of leg lifting.

* * * * *